US008921773B2

(12) United States Patent
Geromanos et al.

(10) Patent No.: US 8,921,773 B2
(45) Date of Patent: Dec. 30, 2014

(54) TECHNIQUES FOR EFFICIENT FRAGMENTATION OF PEPTIDES

(75) Inventors: Scott J. Geromanos, Middletown, NJ (US); Johannes P. C. Vissers, Hulzen (NL); Craig A. Dorschel, Worcester, MA (US); Asish B. Chakraborty, Hopkinton, MA (US); Welbin Chen, Holliston, MA (US); Jeffrey Cruz Silva, Beverly, MA (US)

(73) Assignee: Waters Technologies Corporation, Milford, MA (US)

( * ) Notice: Subject to any disclaimer, the term of this patent is extended or adjusted under 35 U.S.C. 154(b) by 38 days.

(21) Appl. No.: 13/522,779

(22) PCT Filed: Jan. 19, 2011

(86) PCT No.: PCT/US2011/021696
§ 371 (c)(1),
(2), (4) Date: Nov. 5, 2012

(87) PCT Pub. No.: WO2011/091023
PCT Pub. Date: Jul. 28, 2011

(65) Prior Publication Data
US 2013/0105682 A1 May 2, 2013

Related U.S. Application Data

(60) Provisional application No. 61/296,569, filed on Jan. 20, 2010, provisional application No. 61/374,365, filed on Aug. 17, 2010.

(51) Int. Cl.
*H01J 49/00* (2006.01)
*H01J 49/14* (2006.01)
*G01N 30/72* (2006.01)

(52) U.S. Cl.
CPC ........... *H01J 49/0031* (2013.01); *H01J 49/005* (2013.01); *H01J 49/14* (2013.01); *G01N 30/7266* (2013.01)
USPC ................... 250/282; 436/86; 436/87; 436/89

(58) Field of Classification Search
USPC ......................... 250/282, 281; 436/86, 87, 89
See application file for complete search history.

(56) References Cited

U.S. PATENT DOCUMENTS

| 6,621,074 B1 | 9/2003 | Vestal |
| 6,717,130 B2 | 4/2004 | Bateman et al. |
| 6,781,117 B1 | 8/2004 | Willoughby et al. |

(Continued)

FOREIGN PATENT DOCUMENTS

| WO | WO2007/140251 A2 | 12/2007 |
| WO | WO 2007/140327 A2 | 12/2007 |

OTHER PUBLICATIONS

Lange, et al., "Selected reaction monitoring for quantitative proteomics: a tutorial", Oct. 14, 2008 [retrieved from the Internet: <URL: http://www.ncbi.nim.nih.gov./pmc/articles/PMC2583086/>, Mol Syst Biol. 2008, v. 4, pp. 1-20.

*Primary Examiner* — Kiet T Nguyen
(74) *Attorney, Agent, or Firm* — Muirhead and Saturnelli, LLC

(57) ABSTRACT

Techniques are described for performing mass spectrometry. A stream of one or more ions is generated. The stream is transmitted into a collision cell over a period of time. In accordance with a set of criteria including a retention time of one or more precursor ions, a collision energy of the collision cell is selected to generate one or more product ions for said one or more precursor ions in said stream.

11 Claims, 23 Drawing Sheets

(56) References Cited

U.S. PATENT DOCUMENTS

| | | |
|---|---|---|
| 6,833,544 B1 | 12/2004 | Campbell et al. |
| 6,884,995 B2 | 4/2005 | Bateman et al. |
| 7,800,055 B2 * | 9/2010 | Geromanos et al. .......... 250/288 |
| 7,851,742 B2 * | 12/2010 | Geromanos et al. .......... 250/282 |
| 8,143,066 B2 * | 3/2012 | Gorenstein et al. ............ 436/86 |
| 2004/0041090 A1 | 3/2004 | Bloomfield et al. |
| 2007/0158546 A1 | 7/2007 | Lock et al. |
| 2008/0070314 A1 | 3/2008 | Geromanos et al. |

* cited by examiner

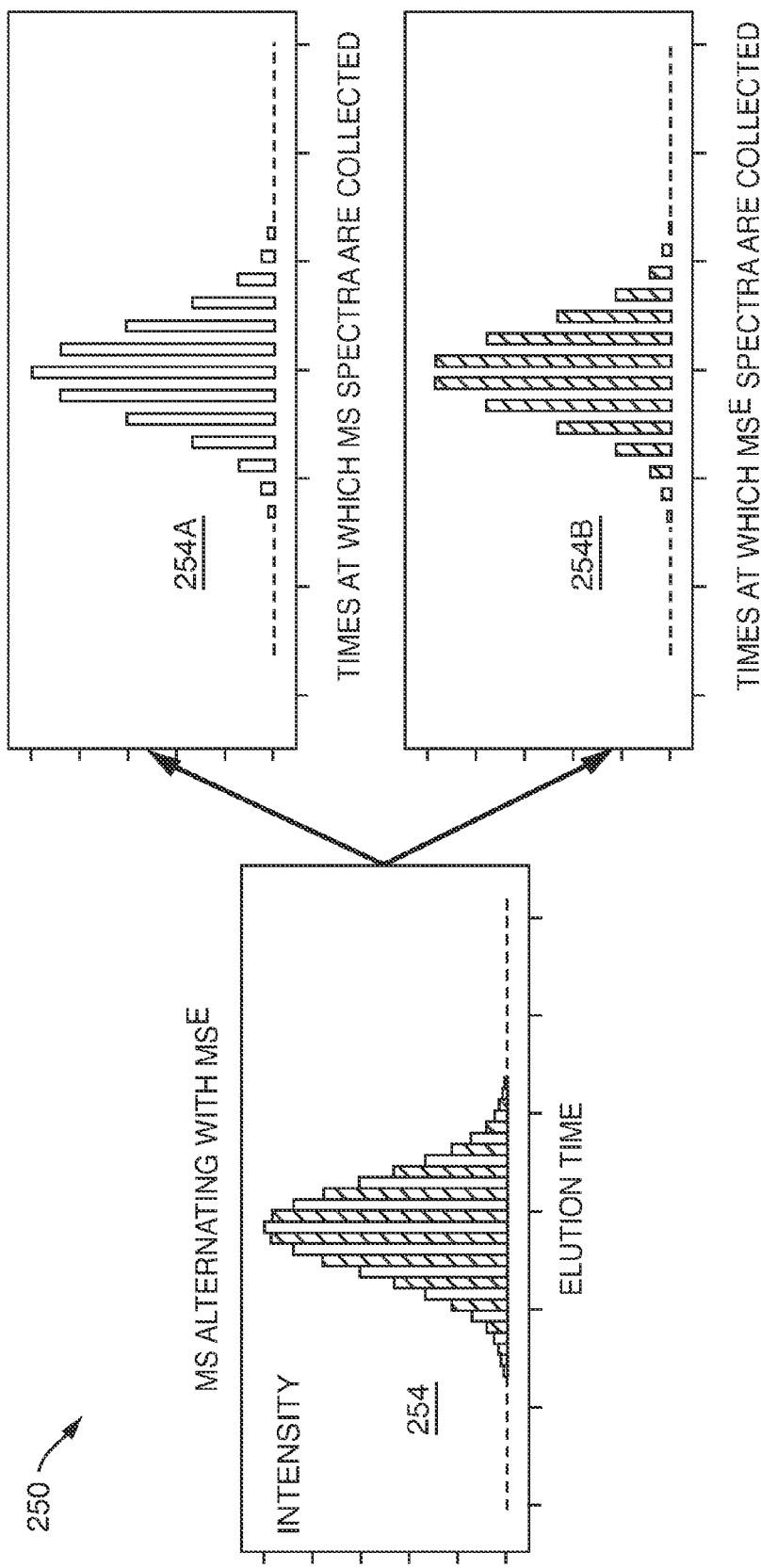

SINGLY CHARGED
300 ↗

| M/Z | RETENTION-TIME (5 MINUTE BINS) | | | | | | | | | | | | | | | | | | | | | | ROW TOTALS |
|---|---|---|---|---|---|---|---|---|---|---|---|---|---|---|---|---|---|---|---|---|---|---|---|
|  | 15 | 20 | 25 | 30 | 35 | 40 | 45 | 50 | 55 | 60 | 65 | 70 | 75 | 80 | 85 | 90 | 95 | 100 | 105 | 110 | 115 | 120 | |
| 400 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 500 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 600 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 1 |
| 700 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 800 | 22 | 10 | 7 | 5 | 6 | 2 | 3 | 1 | 0 | 1 | 1 | 0 | 1 | 0 | 0 | 0 | 0 | 0 | 0 | 0 | 0 | 0 | 65 |
| 900 | 13 | 10 | 3 | 1 | 2 | 2 | 4 | 5 | 2 | 1 | 1 | 0 | 0 | 1 | 0 | 0 | 0 | 0 | 0 | 0 | 0 | 0 | 44 |
| 1000 | 1 | 2 | 3 | 0 | 0 | 0 | 0 | 2 | 2 | 2 | 0 | 2 | 0 | 0 | 0 | 0 | 0 | 0 | 0 | 0 | 0 | 0 | 13 |
| 1100 | 1 | 0 | 0 | 0 | 0 | 0 | 0 | 1 | 0 | 1 | 0 | 0 | 0 | 0 | 0 | 0 | 0 | 0 | 0 | 0 | 0 | 0 | 2 |
| 1200 | 1 | 0 | 0 | 0 | 0 | 0 | 0 | 0 | 1 | 0 | 1 | 0 | 1 | 1 | 0 | 0 | 0 | 0 | 0 | 0 | 0 | 0 | 5 |
| 1300 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 1 |
| 1400 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 1500 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| M/Z | 15 | 20 | 25 | 30 | 35 | 40 | 45 | 50 | 55 | 60 | 65 | 70 | 75 | 80 | 85 | 90 | 95 | 100 | 105 | 110 | 115 | 120 | ROW TOTALS |
|---|---|---|---|---|---|---|---|---|---|---|---|---|---|---|---|---|---|---|---|---|---|---|---|
| 400 | 10 | 10 | 6 | 6 | 1 | 0 | 0 | 2 | 0 | 0 | 0 | 0 | 0 | 0 | 0 | 0 | 0 | 0 | 0 | 0 | 0 | 0 | 36 |
| 500 | 22 | 27 | 36 | 31 | 29 | 24 | 13 | 16 | 9 | 6 | 4 | 0 | 0 | 0 | 0 | 0 | 0 | 0 | 0 | 0 | 0 | 0 | 218 |
| 600 | 28 | 32 | 30 | 28 | 41 | 37 | 26 | 30 | 21 | 17 | 11 | 4 | 2 | 1 | 0 | 0 | 2 | 0 | 0 | 0 | 0 | 0 | 311 |
| 700 | 5 | 16 | 20 | 23 | 23 | 32 | 35 | 23 | 26 | 22 | 17 | 14 | 4 | 0 | 3 | 1 | 0 | 2 | 0 | 0 | 0 | 0 | 268 |
| 800 | 0 | 6 | 4 | 10 | 12 | 21 | 26 | 15 | 25 | 19 | 23 | 25 | 11 | 6 | 11 | 3 | 4 | 2 | 1 | 0 | 0 | 0 | 226 |
| 900 | 2 | 1 | 4 | 4 | 5 | 3 | 12 | 12 | 19 | 16 | 24 | 17 | 14 | 8 | 6 | 7 | 1 | 0 | 0 | 2 | 0 | 0 | 157 |
| 1000 | 0 | 0 | 0 | 0 | 2 | 5 | 6 | 9 | 10 | 10 | 9 | 14 | 12 | 13 | 9 | 4 | 7 | 0 | 0 | 0 | 0 | 0 | 106 |
| 1100 | 0 | 0 | 0 | 0 | 1 | 1 | 2 | 1 | 3 | 5 | 6 | 9 | 5 | 9 | 9 | 2 | 3 | 4 | 2 | 0 | 0 | 0 | 46 |
| 1200 | 0 | 0 | 0 | 0 | 0 | 0 | 0 | 1 | 1 | 1 | 1 | 4 | 1 | 4 | 4 | 4 | 1 | 1 | 0 | 0 | 0 | 0 | 23 |
| 1300 | 0 | 0 | 0 | 0 | 0 | 0 | 0 | 0 | 1 | 0 | 1 | 1 | 2 | 1 | 0 | 2 | 0 | 0 | 0 | 0 | 0 | 0 | 6 |
| 1400 | 0 | 0 | 0 | 0 | 0 | 0 | 0 | 0 | 0 | 0 | 0 | 1 | 0 | 0 | 3 | 0 | 0 | 0 | 0 | 0 | 1 | 0 | 6 |
| 1500 | 0 | 0 | 0 | 0 | 0 | 0 | 0 | 0 | 0 | 0 | 0 | 0 | 0 | 1 | 0 | 1 | 0 | 0 | 0 | 0 | 0 | 0 | 2 |

DOUBLY CHARGED 350

FIG. 5B

TRIPLY CHARGED 400

| M/Z | 15 | 20 | 25 | 30 | 35 | 40 | 45 | 50 | 55 | 60 | 65 | 70 | 75 | 80 | 85 | 90 | 95 | 100 | 105 | 110 | 115 | 120 | ROW TOTALS |
|---|---|---|---|---|---|---|---|---|---|---|---|---|---|---|---|---|---|---|---|---|---|---|---|
| 400 | 2 | 0 | 0 | 1 | 0 | 0 | 0 | 0 | 1 | 0 | 0 | 0 | 0 | 0 | 0 | 0 | 0 | 0 | 0 | 0 | 0 | 0 | 4 |
| 500 | 4 | 3 | 1 | 3 | 0 | 4 | 3 | 0 | 0 | 2 | 0 | 0 | 0 | 0 | 0 | 0 | 0 | 0 | 0 | 0 | 0 | 0 | 22 |
| 600 | 3 | 3 | 2 | 3 | 2 | 8 | 13 | 3 | 8 | 5 | 11 | 4 | 0 | 0 | 0 | 0 | 0 | 0 | 0 | 0 | 0 | 0 | 73 |
| 700 | 1 | 0 | 3 | 2 | 9 | 4 | 6 | 8 | 9 | 4 | 7 | 1 | 1 | 3 | 3 | 0 | 4 | 0 | 0 | 0 | 0 | 0 | 59 |
| 800 | 0 | 0 | 0 | 1 | 3 | 1 | 5 | 4 | 7 | 3 | 2 | 4 | 4 | 4 | 0 | 1 | 1 | 0 | 0 | 0 | 0 | 0 | 38 |
| 900 | 0 | 1 | 0 | 0 | 0 | 0 | 4 | 0 | 0 | 0 | 3 | 4 | 2 | 6 | 5 | 1 | 0 | 0 | 0 | 0 | 0 | 0 | 26 |
| 1000 | 0 | 0 | 0 | 0 | 0 | 0 | 0 | 1 | 0 | 1 | 2 | 1 | 0 | 3 | 5 | 1 | 1 | 0 | 0 | 0 | 0 | 0 | 15 |
| 1100 | 0 | 0 | 0 | 0 | 0 | 0 | 0 | 0 | 0 | 0 | 0 | 0 | 1 | 2 | 2 | 1 | 1 | 1 | 0 | 0 | 0 | 0 | 8 |
| 1200 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 1 |
| 1300 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 1 |
| 1400 | 0 | 0 | 0 | 0 | 0 | 0 | 0 | 0 | 0 | 0 | 0 | 0 | 0 | 0 | 0 | 1 | 0 | 0 | 0 | 0 | 0 | 1 | 2 |
| 1500 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| TOTALS ACROSS ALL 3 CHARGE STATES | 116 | 121 | 121 | 121 | 136 | 148 | 160 | 132 | 149 | 113 | 128 | 106 | 61 | 68 | 55 | 24 | 26 | 10 | 4 | 2 | 0 | 1 | 1802 |

| | CHARGE STATE | | | | | | | |
|---|---|---|---|---|---|---|---|---|
| | 1+ | | 2+ | | 3+ | | 4+ | |
| | MIN CE 1+ | MAX CE 1+ | MIN CE 2+ | MAX CE 2+ | MIN CE 3+ | MAX CE 3+ | MIN CE 4+ | MAX CE 4+ |
| 300 | 13 | 20 | 7 | 16 | 5 | 12 | 5 | 10 |
| 400 | 14 | 22 | 8 | 18 | 6 | 14 | 6 | 12 |
| 500 | 15 | 24 | 9 | 20 | 7 | 16 | 7 | 14 |
| 600 | 16 | 26 | 10 | 22 | 8 | 18 | 8 | 16 |
| 700 | 17 | 28 | 11 | 24 | 9 | 20 | 9 | 18 |
| 800 | 18 | 30 | 12 | 26 | 10 | 22 | 10 | 20 |
| 900 | 19 | 32 | 13 | 28 | 11 | 24 | 11 | 22 |
| 1000 | 20 | 34 | 14 | 30 | 12 | 26 | 12 | 24 |
| 1100 | 21 | 36 | 15 | 32 | 13 | 28 | 13 | 26 |
| 1200 | 22 | 38 | 16 | 34 | 14 | 30 | 14 | 28 |
| 1300 | 23 | 40 | 17 | 36 | 15 | 32 | 15 | 30 |
| 1400 | 24 | 42 | 18 | 38 | 16 | 34 | 16 | 32 |
| 1500 | 25 | 44 | 19 | 40 | 17 | 36 | 17 | 34 |
| 1600 | 26 | 46 | 20 | 42 | 18 | 38 | 18 | 36 |
| 1700 | 27 | 48 | 21 | 44 | 19 | 40 | 19 | 38 |
| 1800 | 28 | 50 | 22 | 46 | 20 | 42 | 20 | 40 |
| 1900 | 29 | 52 | 23 | 48 | 21 | 44 | 21 | 42 |
| 2000 | 30 | 54 | 24 | 50 | 22 | 46 | 22 | 44 |

M/Z VALUES

| | CHARGE STATE 822 ↘ 823 ↙ | | | | | | | |
|---|---|---|---|---|---|---|---|---|
| | 1+ | | 2+ | | 3+ | | 4+ | |
| | MIN CE 1+ | MAX CE 1+ | MIN CE 2+ | MAX CE 2+ | MIN CE 3+ | MAX CE 3+ | MIN CE 4+ | MAX CE 4+ |
| 300 | 8 | 20 | 5 | 16 | 5 | 12 | 5 | 8 |
| 400 | 9 | 22 | 8 | 18 | 6 | 14 | 6 | 10 |
| 500 | 11 | 24 | 8 | 20 | 8 | 16 | 7 | 12 |
| 600 | 12 | 26 | 10 | 22 | 10 | 18 | 8 | 14 |
| 700 | 13 | 30 | 10 | 26 | 10 | 22 | 9 | 18 |
| 800 | 15 | 35 | 10 | 31 | 10 | 27 | 10 | 23 |
| 900 | 19 | 40 | 13 | 36 | 11 | 32 | 11 | 28 |
| 1000 | 22 | 44 | 16 | 40 | 15 | 36 | 12 | 32 |
| 1100 | 25 | 46 | 19 | 42 | 18 | 38 | 13 | 34 |
| 1200 | 27 | 48 | 21 | 44 | 20 | 40 | 14 | 36 |
| 1300 | 28 | 49 | 22 | 45 | 21 | 41 | 15 | 37 |
| 1400 | 28 | 50 | 22 | 46 | 22 | 42 | 16 | 38 |
| 1500 | 28 | 50 | 22 | 46 | 23 | 42 | 17 | 38 |
| 1600 | 28 | 50 | 22 | 46 | 23 | 42 | 18 | 38 |
| 1700 | 28 | 51 | 22 | 47 | 23 | 43 | 19 | 39 |
| 1800 | 29 | 510 | 23 | 47 | 23 | 43 | 20 | 39 |
| 1900 | 29 | 52 | 23 | 48 | 23 | 44 | 21 | 40 |
| 2000 | 30 | 52 | 24 | 48 | 23 | 44 | 22 | 40 |

M/Z VALUES

FIG. 9B

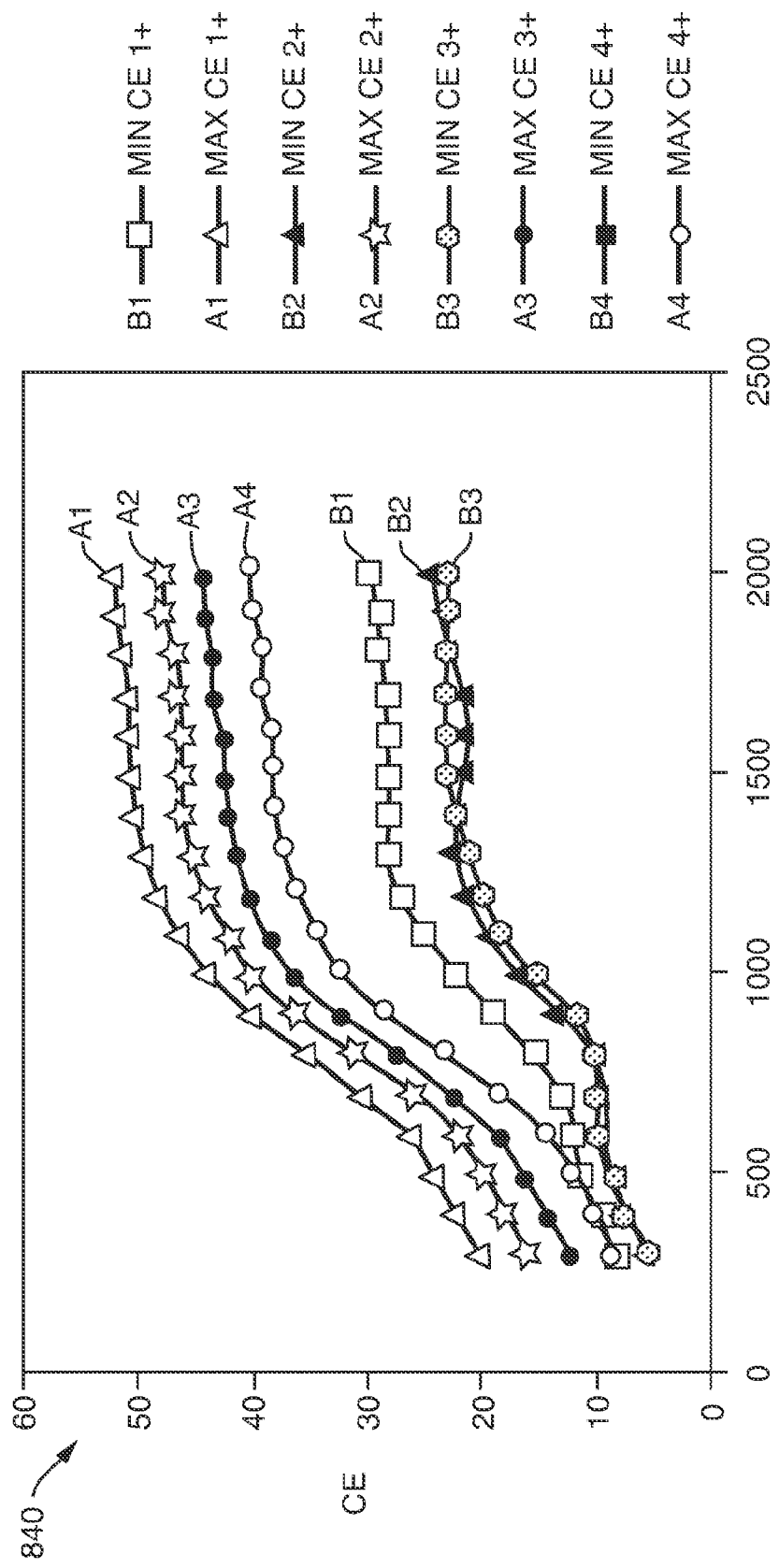

US 8,921,773 B2

TECHNIQUES FOR EFFICIENT FRAGMENTATION OF PEPTIDES

RELATED APPLICATION

This application is a National Stage of International Application No. PCT/US2011/021696, filed Jan. 19, 2011, which claims priority to U.S. Provisional Application No. 61/296,569, filed Jan. 20, 2010 and US Provisional Application No. 61/374,365, filed Aug. 17, 2010, which are hereby incorporated by reference herein.

TECHNICAL FIELD

This application generally relates to techniques for use with analyses of compounds, and, more particularly, to instruments and methods for performing mass spectrometry.

BACKGROUND INFORMATION

Mass spectrometry (MS) is used widely for identifying and quantifying molecular species in a sample. During analysis, molecules from the sample are ionized to form ions. A detector produces a signal relating to the mass of the molecule and charge carried on the molecule and a mass-to-charge ratio (m/z) for each of the ions is determined.

A chromatographic separation technique may be performed prior to injecting the sample into a mass spectrometer. Chromatography is a technique for separating compounds, such as those held in solution, where the compounds will exhibit different affinity for a separation medium in contact with the solution. As the solution flows through such an immobile medium, the compounds separate from one another. Common chromatographic separation instruments include gas chromatographs (GC) and liquid chromatographs (LC). When coupled to a mass spectrometer, the resulting systems are referred to as GC/MS or LC/MS systems. GC/MS or LC/MS systems are typically on-line systems in which the output of the GC or LC is coupled directly to the MS.

In an LC/MS system, a sample is injected into the liquid chromatograph at a particular time. The liquid chromatograph causes the sample to elute over time resulting in an eluent that exits the liquid chromatograph. The eluent exiting the liquid chromatograph is continuously introduced into the ionization source of the mass spectrometer. As the separation progresses, the composition of the mass spectrum generated by the MS evolves and reflects the changing composition of the eluent.

Typically, at regularly spaced time intervals, a computer-based system samples and records the spectrum. The response (or intensity) of an ion is the height or area of the peak as may be seen in the spectrum. The spectra generated by conventional LC/MS systems may be further analyzed. Mass or mass-to-charge ratio estimates for an ion are derived through examination of a spectrum that contains the ion. Retention time estimates for an ion are derived by examination of a chromatogram that contains the ion.

Two stages of mass analysis (MS/MS also referred to as tandem mass spectrometry) may also be performed. One particular mode of MS/MS is known as product ion scanning (and also as data dependent analysis (DDA)) where parent or precursor ions of a particular m/z value are selected in the first stage of mass analysis by a first mass filter/analyzer. The selected precursor ions are then passed to a collision cell where they are fragmented to produce product or fragment ions. The product or fragment ions are then mass analyzed by a second mass filter/analyzer to obtain a resulting product spectrum. The foregoing process can be repeated for other selected precursor ions of interest.

In connection with mass spectrometry and ionizing a precursor ion to produce characteristic fragments thereof, a collision energy (CE) voltage is selected to impart a desired CE to ions transmitted to the collision cell. The CE may be selected, such as from a lookup table of empirically derived CE values, as a function of the precursor's m/z value or mass and charge state. A collision cell may include a chamber into which an inert gas or a mixture of gases is introduced. The CE is imparted by selecting and applying the CE voltage to induce collisions of the molecules of atoms of the gas of the collision cell.

SUMMARY OF THE INVENTION

In accordance with one aspect of the invention is a method for performing mass spectrometry comprising: generating a stream of one or more ions; transmitting said stream into a collision cell over a period of time; and selecting, in accordance with a set of criteria including a retention time of one or more precursor ions, a collision energy of the collision cell to generate one or more product ions for said one or more precursor ions in said stream. The collision energy may be selected in accordance with one or more sets of data respectively associated with said one or more precursor ions, each of said sets of data including a retention time, a mass or m/z value, and a charge state associated with one of said precursor ions. The period of time may correspond to an amount of time of an elevated energy scan associated with producing said one or more product ions from said one or more precursor ions. During the elevated energy scan, the collision energy may be varied from a minimum setting to a maximum setting. The collision energy may be increased during said period of time from said minimum setting to said maximum setting. The collision energy may be increased linearly during said period of time. The collision energy may cause fragmentation of at least one ion. The period of time may include a first amount of time of a low energy scan during which collision energy is not varied, said low energy scan being associated with said one or more precursor ions. During the low energy scan, a spectrum for the first amount of time may correspond to said one or more precursors which are fragmented during a second amount of time included in said period of time when performing an elevated energy scan where said collision energy is varied during said second amount of time. The collision energy may be increased during said second amount of time. The method may also include evaluating, in accordance with one or more fragmentation criteria, whether said one or more precursor ions are sufficiently fragmented during said elevated energy scan when said collision energy is varied from said minimum setting to said maximum setting; and adjusting said minimum setting and said maximum setting in accordance with said evaluating to generate, respectively, any one or more of an adjusted minimum setting and an adjusted maximum setting. The minimum setting and the maximum setting may be used in a first run with a sample and said adjusted minimum setting and said adjusted maximum setting are used in a subsequent run with said sample. The fragmentation criteria may be used to determine whether one or more precursor ions having a same retention time are under fragmented and/or over fragmented. The fragmentation criteria may include a first indicator related to underfragmentation and a second indicator related to overfragmentation.

In accordance with another aspect of the invention is an apparatus for performing mass spectrometry comprising: an ionizer for generating ions; a fragmentation means operable in a first mode at a range of different collision energies from a minimum value to a maximum value wherein, when in the first mode, at least a portion of said ions are fragmented to produce product ions from one or more precursor ions, and a second mode at a second collision energy less than said minimum value energy of said range, said second mode operable to generate a low fragmentation spectrum associated with said one or more precursor ions; a mass analyzer; and a control system which, in use, repeatedly switches said fragmentation means back and forth between said first mode and said second mode, and, when in said first mode for a continuous period of time, selects and switches said fragmentation means between said different collision energies in said range by increasing a current collision energy setting during said period of time from said minimum value to said maximum value. The range used for a first retention time may have a first minimum value and a first maximum value. The range used for a second retention time subsequent to the first retention time may have a second minimum value and a second maximum value, said second minimum value being greater than said first minimum value and said second maximum value being greater than said first maximum value.

In accordance with another aspect of the invention is a method for performing mass spectrometry comprising: selecting a minimum collision energy and a maximum collision energy used during a period of time in which one or more precursor ions are fragmented into one or more product ions; generating said one or more precursor ions using a collision energy less than said minimum collision energy; and setting a collision cell to said minimum collision energy and varying a current collision energy of said collision cell during said period of time from said minimum collision energy to said maximum collision energy to generate said one or more product ions, wherein said minimum collision energy and said maximum collision energy are selected in accordance with a retention time of said one or more precursor ions. For a second period of time subsequent to said period of time, said current collision energy may be varied from a second minimum collision energy to a second maximum collision energy during said second period of time to fragment one or more precursor ions, said second minimum collision energy being greater than said minimum collision energy and said second maximum collision energy being greater than said maximum collision energy. Ions eluting during said period of time may have a first retention time and ions eluting during said second period of time may have a second retention time later than said first retention time. The current collision energy may increase linearly from said minimum collision energy to said maximum collision energy during said period of time. The current collision energy may increase non-linearly from said minimum collision energy to said maximum collision energy during said period of time.

In accordance with another aspect of the invention is a method for performing mass spectrometry comprising: selecting a cone voltage as a function of a retention time associated with each of one or more precursors; and generating a stream of one or more ions using said cone voltage. The cone voltage selected in said selecting may vary at different points in time during a run. A first set of cone voltages may be used in a first run for mass spectral analysis of a sample, each cone voltage in said first set corresponding to a different retention time. The method may further include analyzing data from said first run and accordingly adjusting said first set of cone voltages to generate a second set of cone voltages. The analyzing may include determining whether a measured amount of in-source fragmentation occurring at each of different retention times is in accordance with a threshold. The threshold may be a percentage range and a cone voltage may be increased if a measured amount of in-source fragmentation is less than said threshold and a cone voltage may be decreased if a measured amount of in-source fragmentation is more than said threshold. The second set of cone voltages may be used when performing a second run for mass spectral analysis of said sample. The method may also include analyzing data from said second run and accordingly adjusting said second set of cone voltages to generate a third set of cone voltages. For a first set of data associated with a low energy scan for said one or more precursors having a first retention time and a second set of data associated with a elevated energy scan for one or more product ions which have said first retention time and are fragments of said one or more precursors, said determining whether a measured amount of in-source fragmentation occurring at each of different retention times is in accordance with a threshold may further comprise identifying one or more proteins using said first set of data and said second set of data by determining which precursors of said low energy scan and which product ions in said elevated energy scan match, respectively, to precursors and product ions of said one or more proteins; determining a set of unmatched ions in said low energy scan which have not been matched with a protein by said identifying; and determining whether any of said unmatched ions in said set are in-source fragments of matched precursors from said low energy scan which have been matched with a protein by said identifying. The cone voltage may vary linearly with respect to time. The cone voltage may vary non-linearly with respect to time. The cone voltage may be varied during an elevated energy scan during which precursor fragmentation occurs. The cone voltage may linearly vary during the elevated energy scan. The cone voltage may vary non-linearly during the elevated energy scan.

In accordance with another aspect of the invention is a method of perform mass spectrometry comprising: providing an ion source for generating ions, wherein said ion source uses a cone voltage selected as a function of a retention time associated with each of one or more precursors; and passing said ions to a collision cell operable at a collision energy selected in accordance with a set of criteria including a retention time of said one or more precursor ions. When performing a elevated energy scan to fragment one or more precursor ions and generate one or more product ions, said collision cell may operate at a minimum collision energy at a start of said elevated energy scan and may increase said collision energy to a maximum collision energy at an end of said elevated energy scan. When performing said elevated energy scan, said minimum collision energy and said maximum collision energy may be selected as a function of retention time. A first minimum collision energy and a first maximum collision energy may be selected for use during a first elevated energy scan to generate product ions having a first retention time. A second minimum collision energy and a second maximum collision energy may be selected for use during a second elevated energy scan to generate product ions having a second retention time. The second retention time may be greater than said first retention time, said first minimum collision energy may be greater than said second minimum collision energy, and said first maximum collision energy may be greater than said second maximum collision energy.

In accordance with another aspect of the invention is a computer readable medium comprising code stored thereon for performing mass spectrometry, the computer readable medium comprising code stored thereon that: selects a cone voltage in accordance with a first set of criteria including a retention time associated with one or more ions; and selects a collision energy in accordance with a second set of criteria including a retention time of said one or more ions.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 2B shows three related graphs, which illustrate the collection of mass spectra in accordance with one embodiment of the invention;

FIGS. 5A, 5B and 6 are examples of how precursor ions may be collectively represented in different groupings in an embodiment in accordance with techniques described herein;

FIGS. 9A-9D are exemplary illustrations of collision energy values that may be used in connection with techniques herein;

DESCRIPTION

Figure 1:
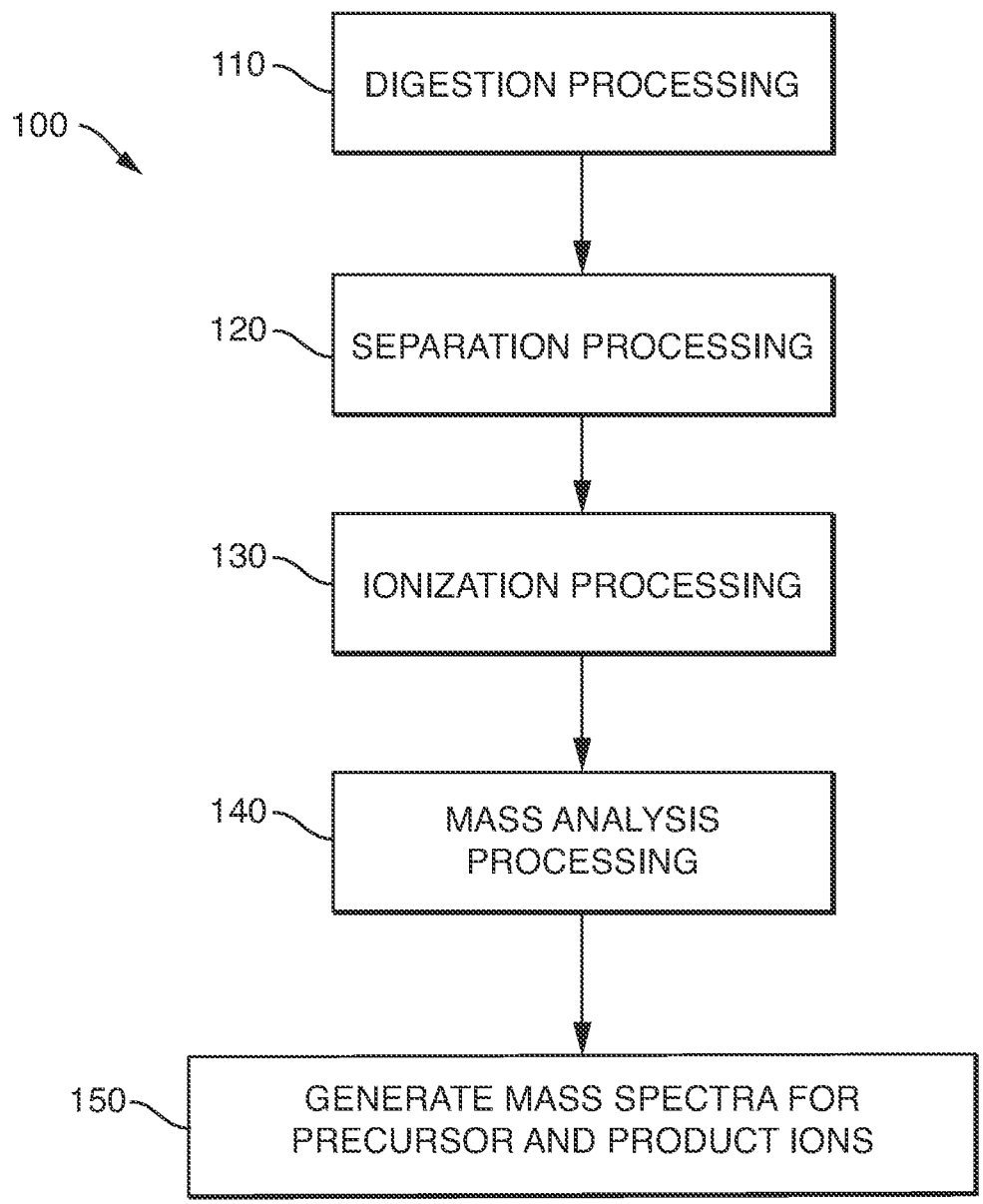
FIG. 1 is a flow diagram of a method for performing chemical analyses of compounds, in accordance with one embodiment of the invention.

As used herein, the following terms generally refer to the indicated meanings:

Protein—a specific primary sequence of amino acids assembled as a single polypeptide.

Peptide—a specific sequence of amino acids assembled as a single polypeptide contained within the primary sequence of a protein.

Tryptic peptides—peptides generated from a protein sequence that result from enzymatic cleavage of the protein by trypsin. In the ensuing description, digest peptides are referred to as tryptic peptides for convenience. It should be understood, however, that embodiments of the present invention apply to other peptide digestion techniques. Moreover, the term "digestion" is used herein to refer generally to any suitable method for degrading or cleaving a polypeptide, including, for example, the use of cellular enzymes (proteases) and intramolecular digestion. The term "proteolytic," as used herein, refers to any enzyme which digests or lyses large proteins into smaller sections or amino acids.

Precursor peptides—tryptic peptides (or other protein cleavage products) that are generated using a protein-cleavage protocol. The precursors are optionally separated chromatographically and passed to a mass spectrometer. An ion source ionizes these precursor peptides to typically produce a positively charged, protonated form of the precursor. The mass of such positively charged protonated precursor ion is herein referred as the "mwHPlus" or "MH+" of the precursor. In the following, the term "precursor mass" refers generally to the protonated, mwHPlus or MH+ mass of the ionized, peptide precursor.

Fragments or product ions—Multiple types of fragments or product ions can occur in LC/MS analyses. In the case of tryptic peptide precursors, fragments can include polypeptide ions that are produced from collisional fragmentation of the intact peptide precursors and whose primary amino acid sequence is contained within the originating precursor peptide. Y-ions and B-ions are examples of such peptide fragments. Fragments of tryptic peptides can also include immonium ions, functional groups such as a phosphate ion ($PO_3$), mass tags cleaved from a specific molecule or class of molecules, or "neutral loss" of water ($H_2O$) or ammonia ($NH_3$) molecules from the precursor.

Y-ions and B-ions—If a peptide fragments at the peptide bond, and if a charge is retained on the N terminal fragment, that fragment ion is termed a B-ion. If the charge is retained on the C terminal fragment, the fragment ion is termed a Y-ion. A more comprehensive list of possible fragments and their nomenclature is provided in Roepstorff and Fohlman, Biomed Mass Spectrom, 1984; 11(11):601 and Johnson et al, Anal. Chem 1987, 59(21): 2621:2625.

Retention time—in context, typically refers to the point in a chromatographic profile at which an entity reaches its maximum intensity.

Ions—each peptide typically appears in an LC/MS analysis as an ensemble of ions due to the natural abundance of the isotopes of the constituent elements. An ion has a retention time and an m/z value. The mass spectrometer (MS) detects only ions. The LC/MS technique produces a variety of observed measurements for every detected ion. This includes: the mass-to-charge ratio (m/z), mass (m), the retention time, and the signal intensity of the ion, such as a number of ions counted.

MwHPlus—The neutral, monoisotopic mass of the peptide plus the weight of one proton, 1.007825 amu.

Generally, an LC/MS analysis optionally provides an empirical description of a peptide in terms of its mass, charge, retention time and total intensity. When a peptide elutes from the chromatographic column, it elutes over a specific retention time period and reaches its maximum signal at a single retention time. After ionization and (possible) fragmentation, the peptide appears as a related set of ions. The different ions in the set correspond to different isotopic compositions and charges of the common peptide. Each ion within the related set of ions produces a single peak retention time and peak shape. Since these ions originate from a common peptide, the peak retention time and peak shape of each ion is identical, within some measurement tolerance. The MS acquisition of each peptide produces multiple ion detections for all isotopes and charge states, all sharing the same peak retention-time and peak shape within some measurement tolerance.

In an LC/MS separation, a single peptide (precursor or fragment) produces many ion detections, which appears as a cluster of ions, at multiple charge states. Deconvolution of these ion detections from such a cluster, indicates the presence of a single entity of a unique monoisotopic mass, at a specific retention time, of a measured signal intensity, in a charge state.

Techniques and embodiments will now be described with reference to exemplary methods and apparatus for analyzing samples such as may be for polypeptide analyses in a system performing mass spectroscopy. It will be appreciated that the techniques described herein for use when performing mass spectroscopy may be used in connection with other embodiments and have broader application for analysis of other compounds such as in proteomics, metabonomics, and the like.

Referring to FIG. 1, shown is a flow diagram of a method 100 for performing chemical analyses of compounds as may be performed in an embodiment in connection with the techniques herein. The method 100 includes digesting 110 one or more compounds of a reference sample into component fragments of the compounds, separating 120 the components, ionizing 130 and mass analyzing 140 at least some of the separated components, and generating 150 mass spectra for the precursor and product or fragment ions of at least one compound in the sample. The generated mass spectra may be further analyzed and/or processed for use in connection with any of a variety of techniques for different applications.

Some uses of the method 100 are directed toward protein-related analyses. Thus, for convenience, the following description refers to proteins and related fragments, and utilizes examples of analyses of compounds that are polypeptides, such as proteins; in these examples, a protein is digested into component fragments that are precursor fragments of the protein. Precursors, in turn, are ionized to form precursor ions which are then fragmented into product ions in preparation for mass analysis.

Digesting 110 is accomplished via any suitable technique for cleaving proteins, including known techniques. For example, as described above, a protein is digested into precursor polypeptides or amino acids through use of one or more enzymes such as trypsin. A precursor may be optionally used in additional analyses subsequent to chromatographic separation. As described in more detail below, precursors are optionally ionized and/or further fragmented into product fragments.

Separating 120 is accomplished by any suitable chromatographic-related technique, including known techniques such as reverse-phase chromatography, gel-permeation chromatography, size-exclusion chromatography, and electrophoresis. Separating 120 provides values associated with retention times of the proteins and/or precursors obtained from digesting 110 proteins in a sample.

In preparation for mass analyzing 140 the eluent from the separating 120 process (e.g., such as a chromatographic separation) is subjected to an ionizing 130 process. Any suitable ionizing 130 process is optionally used, including known techniques such as electrospray ionization and MALDI. During the ionizing 130 process, at least some of the precursors are ionized to form precursor ions. For example, a single protein molecule is digested 110 to form twenty precursor fragments, of which ten are ionized during ionizing 130. As described in more detail below, precursors may be further fragmented to obtain product ions such as through the use of a collision cell.

Mass analyzing 140 provides values associated with mass and values associated with ion intensity of the precursor ions. Mass analyzing 140 is performed via any suitable mass-analysis techniques, including known techniques. Such techniques include magnetic-sector spectrometry and time-of-flight spectrometry.

As illustrated in step 150, information obtained from the above-described analysis step 140 may be in the form of mass spectra for the precursor and product ions used to obtain an input data set which may be further processed.

In some embodiments performing the steps of FIG. 1, the mass spectra data generated in step 150 may be obtained using an LC/MS system. For example, as described in more detail with reference to FIGS. 2A and 2B, an eluent output by the liquid chromatograph is introduced into a mass spectrometer through an electrospray interface. Optionally, a first quadrupole of a multi-quadrupole MS instrument functions as an ion guide. An alternating voltage is applied to a collision cell (such as 218 of FIG. 2A) of the instrument. Spectra are collected of precursors ions and of their fragment (product) ions, for example, in an alternating fashion, as described below.

Preferably, both precursor ions and associated product ions are formed from the same precursor material obtained from the separating 120 process. In this manner, both precursor ions and associated product ions will have the same retention time data determined from the separating 120 process.

Any suitable method, including known methods, may be used to obtain both precursor and product ions from a single sample injection. Such methods provide effectively simultaneous mass analysis of both precursor and product ions. For example, a portion of an eluted precursor is fragmented to form product ions, and the precursor and product ions are substantially simultaneously analyzed, either at the same time or, for example, in rapid succession.

As an alternative example, two or more alternating portions of the peak are used respectively for precursor and product analysis. A portion of a peak's precursor material is ionized and analyzed, and then a next portion is dissociated into product fragments that are analyzed. In one embodiment, alternating portions of an eluting precursor are sampled to alternately obtain data for the precursor ion and its product ions. The obtained data permits reconstruction of a peak shape to permit measurement of an accurate retention time value for both the eluted precursor and its associated product. Moreover, for example, peak shape, width, and/or time of reconstructed peaks associated with precursor ions and with product ions are optionally compared to determine which product ions are associated with a particular product ion.

One approach to such alternating, effectively simultaneous analysis, is described in U.S. Pat. No. 6,717,130 to Bateman, et al. ("Bateman"), which is incorporated herein by reference and describes application of an alternating voltage to a collision cell to regulate fragmentation. In accordance with an aspect of the techniques described herein in following paragraphs, the techniques described in the Bateman '130 patent may be further modified by varying in an incremental manner the CE voltage applied during each high or elevated energy single scan containing primarily fragment ions associated with one or more unfragmented precursors contained in a prior low energy scan. Additional description of related features is provided below. Thus, an embodiment may use a modification of the technique described in the Bateman '130 patent or other suitable technique which may use retention-time observations to support the determination of which product ions are derived from a particular precursor. The product ions are associated with their precursor ion in response to matching retention-time values.

For example, a threshold retention-time difference is selected; if the difference in retention times of a product ion and a precursor ion is less than the threshold value, the product is determined to be derived from the precursor. For example, one suitable threshold value is equal to one tenth the retention-time peak width of the precursor ion. The retention-time value of an ion is optionally defined as the time value of the peak maximum of the peak that was observed for that ion.

Figure 2A:
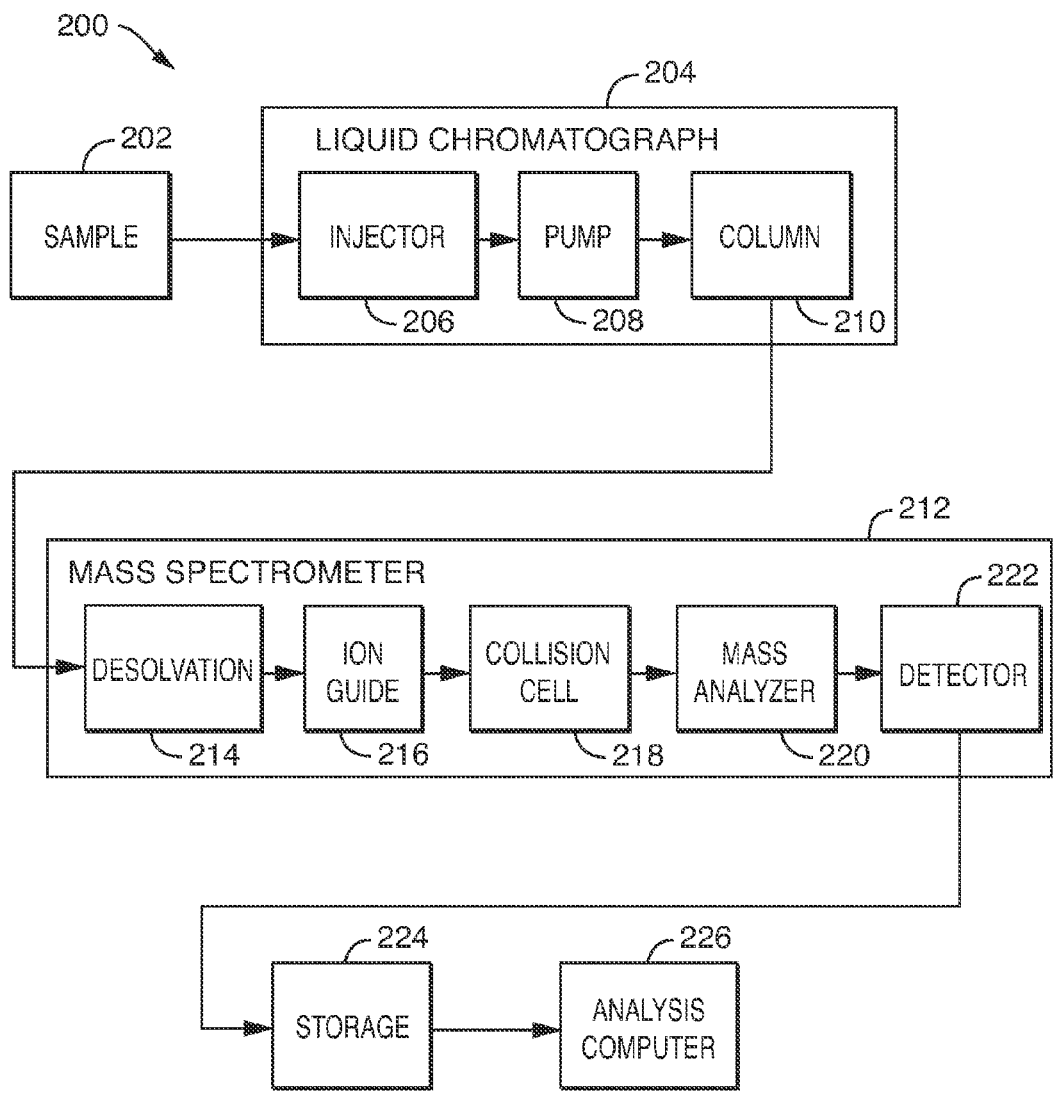
FIG. 2A is a block diagram of an LC/MS system, in accordance with one embodiment of the invention.

Referring to FIGS. 2A and 2B, some embodiments of the techniques herein relate to LC/MS instruments. FIG. 2A is a block diagram of an LC/MS system 200, according to one embodiment of the present invention. The instrument includes a chromatography module 204 and a mass-spectrometer module 212 that receives an eluent from the chromatography module 204. The LC module 204 includes an injector 206 that receives a sample 202, a pump 208 and a column 210. The MS module 212 includes a desolvation/ionization device 214, an ion guide 216, a mass analyzer 220, and a detector 222. The system 200 also includes a data storage unit 224 and a computer module 226. In operation, the sample 202 is injected into the LC module 204 via the injector 206. The pump 208 pumps the sample through the column 210 to separate the mixture into component parts according to retention time through the column 210.

The output from the column 210 is input to a mass spectrometer 212 for analysis. Initially, the sample is desolvated and ionized by the desolvation/ionization device 214. Any desolvation technique can be employed, including, for example, a heater, a gas, and a heater in combination with a gas or other desolvation technique. Ionization can be by any suitable ionization technique, including for example, electrospray ionization (ESI), atmospheric pressure chemical ionization (APCI), or other ionization technique. Ions resulting from the ionization are fed to a collision cell 218 by the ion guide 216.

The collision cell 218 is used to fragment the ions. In some embodiments, the collision cell 218 is operated in a switching mode to support observation of both precursor ions and product ions of the same eluting precursor material.

Any suitable switching techniques may be used, including known techniques. Some embodiments may use a fragmentation protocol in which a relatively simple alternating voltage cycle is applied to the cell 218. This switching is done at a high enough frequency so that multiple elevated and multiple low-energy spectra are contained within a single chromatographic peak. Unlike some other switching protocols, the cycle is independent of the content of the data.

For example, as described in the Bateman '130 patent, an alternating voltage is applied to the collision cell 218 to cause fragmentation. Spectra are collected for the precursors (no collisions) and fragments (results of collisions.)

Alternative embodiments may utilize other means for fragmentation, such as any suitable collision fragmentation or reaction device, where a CE voltage can be applied and varied in accordance with techniques described herein.

The output of the collision cell 218 is input to a mass analyzer 220. The mass analyzer 220 is any suitable mass analyzer, including quadrupole, time-of-flight (TOF), ion trap, magnetic sector mass analyzers as well as combinations thereof. The detector 222 detects ions emanating from the mass analyzer 220. The detector 222 is optionally integral with mass analyzer 220. For example, in the case of a TOF mass analyzer, the detector 222 is optionally a microchannel plate detector that counts intensity of ions, i.e., counts numbers of impinging ions. The storage medium 224 provides permanent storage for storing the ion counts for analysis. For example, storage medium 224 is an internal or external computer disk. The analysis computer 226 analyzes the stored data. Data can also be analyzed in real time without requiring storage in a storage medium 224. In that case, the detector 222 passes data to be analyzed directly to computer 226 without first storing it to permanent storage.

The collision cell 218 performs fragmentation of the precursor ions. Fragmentation can be used to determine the sequence of a peptide and subsequently lead to the identity of the originating protein. The collision cell 218 may utilize an inert gas, such as nitrogen within a pressurized chamber. When a charged peptide interacts with the gas' atoms, the resulting collisions can fragment the peptide by breaking it up at one or more characteristic bonds. The most common resulting fragments are described as Y- or B-ions. Such fragmentation can be accomplished as on-line fragmentation by switching the voltage in a collision cell between a low voltage state (low energy (LE) such as used during an LE scan) which obtains MS spectra of the peptide precursor, with a high voltage state (high or elevated energy (EE) such as used during an EE scan) which obtains MS spectra of the collisionally induced fragments of the precursors. High and low voltages are referred to, respectively, as high or elevated energy and low energy, since a voltage is used to impart kinetic energy to an ion. Such techniques using alternating LE and EE consecutive scans are described in the Bateman '130 patent.

The chromatographic module 204 includes any suitable chromatography instrument(s), including known instruments, such as column-based instruments. Suitable columns include columns known to one having ordinary skill in the chromatographic arts. The column can be formed from, for example, metallic or insulating materials. Suitable materials include known materials such as steel, fused silica, or lined materials. The column can include more than one column, disposed in serial and/or parallel configurations. For example, the column can be a capillary column and can include multiple capillary tubes.

The computer module 226 is in data communication with other components of the system 200 via wired and/or wireless means, such as those known in the data-communication arts. The module 226 receives process data, for example, from the mass-spectrometer module 212, and provides control signals. The module 226 is optionally configured to implement methods described herein, such as the method 100 for chemical analysis described above, and/or the different techniques described herein for further processing the input data set acquired as a result of the step 150 of FIG. 1. The module 226, in various illustrative embodiments, is implemented in software, firmware, and/or hardware (e.g., as an application-specific integrated circuit), and includes, if desired, a user interface. The module 226 includes and/or is in communication with storage component(s), such as the storage unit 224.

Suitable implementations of the module 226 include, for example, one or more integrated circuits, such as microprocessors. A single integrated circuit or microprocessor in some alternative embodiments includes the module 226 and other electronic portions of the system 200. In some embodiments, one or more microprocessors implement software that enables the functions of the module 226. In some embodiments, the software may be executable code which is stored on a computer-readable medium and designed to run on general-purpose equipment and/or specialized processors dedicated to the functionality herein described.

A control means (not shown) provides control signals for the various power supplies (not shown) which respectively provide the necessary operating potentials for the components of the mass spectrometer (e.g., elements 214, 216, 218, 220 and 222). These control signals determine the operating parameters of the instrument, for example the operation of the analyzer 220. The control means is typically controlled by signals from a computer, such as the analysis computer 226, which may also be used to process the mass spectral data acquired. The computer 226 may also display and store mass spectra produced and receive and process commands from an operator. The control means may be automatically set to perform various methods and make various determinations without operator intervention, or may optionally require operator input at various stages.

The control means may also be configured to switch the collision cell 218 back and forth between at least two different modes such as for use in accordance with an alternating LE-EE scanning technique described in the Bateman '130 patent. In a first mode, a relatively high voltage (such as more than 15V) is applied to the collision cell which is sufficient to cause a fair degree of fragmentation of ions passing therethrough. In a second mode a relatively low voltage (such as less than or equal to 5V) is applied which causes relatively little (if any) significant fragmentation of ions passing therethrough. The control means may switch between modes such as approximately every second. As described elsewhere herein, the second mode may be used in connection with generating a spectrum for one or more precursor ions which are then fragmented at a next subsequent point in time when operating in the first mode generating another spectrum of one or more related product ions. Furthermore, in accordance with techniques described herein, the control means may also automatically control and further vary the voltage applied to the collision cell. For example, when operating in the first mode (EE) producing a product ion spectrum, the control means may also vary the voltage applied to the collision cell as a function of time over the course of an experiment resulting in different CEs for the collision cell and ions transmitted thereto. In one embodiment as described elsewhere herein in more detail, the CE may be varied when performing a single EE scan from a minimum setting to a maximum setting so that the CE applied within a time period of the single EE scan when operating in the first mode increases from the minimum to the maximum setting during the time period.

A molecule in an eluent that is separated by a chromatographic separation, and elutes from the column is referred to as the common eluting molecule or originating molecule. As described above, the originating molecule is ionized through the ionization source of the mass spectrometer. The resulting ions are measured in an LC/MS or LC/MS$^E$ spectra. It should be noted that depending on the context, LC/MS may generally refer to the LC/MS process of data acquisition. In connection with data collected and represented such as in the form of spectra, for example, as in connection with FIG. 2B described herein, MS spectra may refer to spectra from unfragmented precursors. MS$^E$ spectra may refer to elevated-energy spectra (i.e., spectra from fragmented precursors, that is, product ions, labeled "MS$^E$"). As a result of isotopic composition and or fragmentation processes, each originating molecule can give rise to multiple categories of ions, each having a unique value of mass and charge. The ion corresponding to the originating molecule is termed the precursor ion, or just the precursor.

In peptide digests the originating molecule is a peptide and the ion corresponding to the peptide is referred to as the precursor. Any ion derived from the originating molecule, whether the precursor or a fragment, must have the same retention time and chromatographic peak profile as the precursor.

In an LC/MS experiment, an ion can be described and/or referred to by its retention time, mass-to-charge ratio or mass, charge state, and intensity. Such information characterizing an ion may be determined using techniques as described in PCT Publication No. WO2007/140327 published Dec. 6, 2007 (PCT application no. PCT/US07/69784, international filing date May 25, 2007), ION DETECTION AND PARAMETER ESTIMATION FOR N-DIMENSIONAL DATA, Gorenstein et al., which is incorporated by reference herein, where the foregoing information for an ion may be determined with respect to the monoisotopic variation of the ion and its determined apex of a chromatographic peak. A single molecule can appear in an LC/MS chromatogram as a cluster of ions. A peptide gives rise to one or more ion clusters. Each cluster corresponds to a different charge state (e.g., Z=1 or Z=2). Each ion in a cluster corresponds to a different isotopic composition of the peptide. In a cluster of ions from a common peptide, the monoisotope is the ion having the lowest mass, where all the isotopes are in their most abundant, low mass state. Since the ions in the cluster come from a common originating molecule, they must share a common retention time and peak profile.

An originating molecule can give rise to multiple ions due to isotope and charge effects. Additional, important sources of ions are fragments of the originating molecule. These fragments arise from processes that break up the originating molecule. These processes can occur in the ionization source or in a collision cell. Because fragment ions derive from a common eluting, originating molecule, they must have the same chromatographic retention time and peak profile as the originating molecule. The retention time and peak shapes of ions that derive from a common originating molecule are the same because the time of ion formation, fragmentation, and ion detection is generally much shorter then the peak width of the originating molecule. For example, a typical chromatographic peak width, measured at full-width at half-maximum (FWHM) is 5 to 30 seconds. The time of ion formation, fragmentation, and detection is typically sub milliseconds. Thus on a chromatographic time scale, the time of ion formation is an instantaneous process. It follows that differences in observed retention times of the ions that derived from an originating molecule is effectively zero. That is, sub-millisecond retention time differences between ions that derived from an originating molecule are small compared to the chromatographic peak width.

The ions that are associated with an originating molecule fall into one of several categories. An ion derived from an originating molecule can be a precursor, a fragment of the precursor, or a fragment of a fragment, or a neutral loss of any of the above masses. Any of these masses can be seen in one or more discrete isotopic states, and in one or more charge states.

In the case of peptides, a given peptide is generally seen to be a cluster of ions, each in a distinct isotopic state, and each in one or more charge states. Ideally the ionization source produces precursors that are a protenated form of the neutral originating molecule. One or more protons can be attached to the neutral molecule and thus the precursors can be one or more mass units higher than the neutral with charge Z=+1, or +2, etc. In practice, this precursor (termed mwHPlus) may be accompanied by lower mass entities that result from the loss of neutral molecules such as water, ammonia, or phosphate. Fragmentation can occur in the source, yielding, typically, Y- or B-ions. As described in connection with techniques herein, fragmentation can be also be deliberately induced by downstream interactions with gas molecules in a collision cell.

With respect to ions that are generated from collision-induced disassociation of intact precursor ions, the fragment product ions are associated with their parent precursor ion. By using the mass spectrometer in a high-low data acquisition mode (also referred to herein as an elevated-low-data acquisition mode) as described in the Bateman '130 patent, this association is accomplished without requiring the instrument to pre-select a single precursor for subsequent fragmentation. More specifically, associated ions are appropriately grouped when multiple precursors are fragmenting simultaneously, at essentially the same retention time.

The retention time and chromatographic peak profile of a molecule (peptide, metabolite, natural product) eluting from a chromatographic support matrix, such as column 210, is a function of the physical interaction of that molecule between the support matrix and mobile phase. The degree of interaction that a molecule has between the support matrix and the mobile phase dictates the chromatographic profile and retention time for that molecule. In a complex mixture, each molecule is chemically different. As a result, each molecule can have a different affinity for the chromatographic matrix and the mobile phase. Consequently, each can exhibit a unique chromatographic profile.

Generally, a chromatographic profile for a specific molecule is unique and describes the physicochemical properties of that molecule. Parameters optionally used to characterize the chromatographic peak profile of a given molecule include the time of initial detection (liftoff), normalized slope, the time of inflection points relative to the time of the peak apex, the time of maximum response (peak apex), the peak width, at inflection points, at full-width-at-half-maximum (FWHM), peak shape asymmetry, and the time of the final detection (touch down) to name only a few.

FIG. 2B shows three related graphs that illustrate the collection of mass spectra during a period of time that covers an eluted peak of a precursor, according to one embodiment of the invention. A first graph 254 illustrates the alternating collection over elution time of low-energy spectra (i.e., spectra from unfragmented precursors, labeled "MS") and elevated-energy spectra (i.e., spectra from fragmented precursors, that is, product ions, labeled "$MS^E$".) Second and third graphs 254A, 254B respectively illustrate the MS and $MS^E$ spectral collection times and the reconstruction of the retention time peak associated with the precursor as may be generated using the alternating scanning technique described in the Bateman '130 patent as further modified in accordance with techniques herein to vary the CE applied for each EE scan (such as by increasing the initial or starting CE applied in each EE scan as the retention time increases with each EE scan) and also vary the CE within each EE scan time period (such as by increasing the CE within a single EE scan).

The reconstructed peak represents the chromatographic elution profile of a single precursor. The horizontal axis corresponds to elution time of the peak profile. The vertical axis corresponds to arbitrary units of intensity associated with the time-varying concentration of the precursor as it elutes from the chromatographic column.

An eluting precursor, passed to the mass spectrometer, thus produces ions in both low- and elevated-energy modes. The ions produced in the low-energy mode are primarily those of the precursor ions in possibly different isotopic and charge states. In proteomic studies, the precursor ions are peptides generated from enzymatic digestion (typically a tryptic digest) of the intact protein(s). In elevated-energy mode, the ions are primarily different isotopes and charge states of the fragment, or product, ions of those precursors. High-energy mode can also be referred to as elevated-energy mode.

In the graph 254, the alternating white and black bars thus represent the times at which spectra are collected with low and high (or elevated)-energy voltages of the eluting chromatographic peak. The low-energy (LE) graph 254A depicts the times at which a low-energy voltage is applied in the collision cell 218, resulting in low-energy spectra. The high or elevated energy (EE) graph 254B depicts the times at which an elevated-energy voltage is applied in the collision cell 218, resulting in elevated-energy spectra. In connection with one embodiment of the techniques herein, the CE may be varied from a minimum value to a maximum value for the time period of a single elevated energy scan. Additionally, the minimum CE value and/or maximum CE value for each subsequent EE scan may be increased as the retention time increases. More generally, the minimum CE value and/or maximum CE value for a given EE scan may be varied as the gradient elution time increases.

In connection with techniques described herein, an embodiment may determine masses of particular precursors of interest using a variety of different techniques. For example, in one embodiment utilizing the Bateman techniques as described elsewhere herein, the low energy (LE) cycle or mode may be used to generate spectra containing ion primarily from unfragmented precursors while the elevated-energy (EE) spectra contain ions primarily from fragmented precursors or product ions.

For a given collision gas at a particular pressure, the optimum CE voltage for collision induced fragmentation such as in the collision cell generally varies with respect to the mass and charge state of the ion to be fragmented. Other factors of the precursor ion to be fragmented which affect the optimum CE desired for fragmentation include the composition of the ion to be fragmented. Ion composition relates, for example, to the number and/or type of amino acids comprising the ion. The amount of energy required to cause sufficient fragmentation by breaking peptide bonds varies with this composition for each ion as the ion elutes. If there are two different ions having different retention times but the same mass and possibly the same charge state, the composition of the ions differs from one another so that a different CE may be desired for each of the two ions in order to adequately fragment both ions. Thus, the retention time associated with a precursor ion may be used to adjust or select a CE utilized during an EE scan in order to adequately fragment the precursor. For example, for two precursor ions having the same mass and charge state but different retention times, it may be determined that a first of the two ions having the earlier retention time has a first CE and a second of the two ions having a later retention time may have a second CE determined as an adjusted value (e.g, incrementally) relative with respect to the first CE for adequate fragmentation. Generally, the more complex the composition (e.g., longer the polypeptide chain, stronger and more complex bonds), the greater the amount of CE needed for adequate fragmentation for a given charge state. Peptides of higher mass and lower charge states use a larger CE to impart sufficient fragmentation. Peptides of higher mass and higher charge states use less CE for sufficient fragmentation. If, for example, one considers a charge state of z=2, the CE needed to impart sufficient fragmentation increased with retention time.

Ions which coelute (having a same retention time) may have varying charge states, masses and/or amino acid composition. Additionally a precursor ion eluting at a given retention-time may exist at multiple charge-states each with its own optimum CE. Therefore the optimum CE for adequate fragmentation of each precursor ion which coelutes at a point in time may vary with each eluting ion and there may be multiple different optimal CEs for a single point in time for the different coeluting precursors. In an embodiment of the techniques described herein using a modified version of the Bateman '130 patent, multiple precursors having a same retention time may be included in a single LE scan and the CE, or range of CE's selected for an associated EE scan to fragment the precursors may be based collectively on characteristics of the multiple coeluting precursors.

Furthermore, the inventors note that masses of ions tend to increase as the time during which an LC/MS or other experiment is run increases. In other words, ions of lesser masses tend to elute earlier and thus have earlier retention times than other ions of larger masses. The inventors also note that an increase in ion mass is typically associated with changing ion composition that tends to be associated with an increase in hydrophobicity. In other words, hydrophobicity tends to increase during the time course or elution time of the experiment so that ions having later retention times tend to have an increase in hydrophobicity in comparison to other ions having earlier retention times. As hydrophobicity increases, higher CEs are often needed for efficient fragmentation. Furthermore, it is noted that as ion mass increases, there is also an increased tendency to obtain multiple charge states due to the increased length and compositional properties that are more typical at higher masses. A peptide can elute at a retention time at multiple charge states (e.g., $MH^+$, $MH^{+2}$ and $MH^{+3}$). Ions of similar length having higher charge states are generally easier to fragment than those of lower charge states. For example, a first precursor ion at charge state=1 requires a higher CE for efficient fragmentation than the first precursor ion at a charge state=2. Precursor ions having higher charge states tend to occur with increased retention time. Precursor ions having lower charge states tend to occur at earlier retention times.

In summary, as an ion's retention time increases, the following also have a tendency to increase: the ion's mass, the charge state for the ion eluting at the retention time, and the hydrophobicity of the ion. With respect to charge state, the frequency or number of ions having higher charge states tends to increase with retention time.

Insufficient CE may not induce fragmentation at all or produce too few fragment ions, for example, that may be needed to identify the structure of the molecule. Additionally, excessive energy may cause excessive or over-fragmentation adversely effecting the identification process. As known in the art, different techniques may be used in connection with identifying peptides and/or proteins based on a degree of matching between precursors and related product ions of an analyzed sample and those stored in a database containing information on known peptides and/or proteins. Thus, insufficient fragmentation of precursors as well as over fragmentation may adversely affect the ability to accurately perform such identifications. It should be noted that a database containing information used to identify proteins may be more generally any data store which may be used to store such information.

In accordance with one aspect of the techniques herein in an embodiment modifying the techniques described in the Bateman '130 patent, the CE voltage selected may be varied during the course of a single EE scan when fragmentation of one or more precursors is expected to occur. The CE may be varied between a minimum and a maximum value during the EE scan as a function of duration or lapsed time (elution time) of the experiment. The CE may be increased during the single EE scan from the minimum to the maximum value in a linear or non-linear fashion. As will be described in more detail below, the CEs during the single EE scan may be determined by selecting CEs based on a linear interpolation using the minimum and maximum values, respectively, as start and ending points for a line. Factors (such as the duration or lapsed time (elution time) of the experiment corresponding to retention time of eluting ions) used in determining a CE (such as during an EE scan in accordance with techniques herein) may be referred to more generally as criteria.

The selected minimum and maximum values for a single EE scan may vary in accordance with, or as a function of, criteria including the masses, charge states, and retention time(s) associated with precursor ions eluting during an LE scan containing the originating precursors. Other aspects of the precursor that may be used in connection with the techniques herein as criteria in combination with the foregoing may relate to precursor intensity and/or precursor composition.

It should be noted that described herein are examples of how different aspects of the foregoing criteria for originating precursors may be used in connection with selecting a CE or range of CEs for use with an EE scan containing product ions associated with the originating precursors. However, it will be appreciated by those of ordinary skill in the art that the general principles described herein have broader applicability in selecting CEs associated with the collision cell when performing other data acquisition techniques.

In an embodiment described in more detail below, the CE imparted to the collision cell when fragmentation data is collected may be ramped from a minimum value to a maximum value for the duration of time of each EE scan. The foregoing may be performed with the expectation that a significant portion of the precursor ions will be optimally fragmented. In the case of peptides as described above, the CE required for efficient fragmentation is related to the mass, charge state, and retention time. An embodiment may use the foregoing alone or in combination with other criteria (such as related to ion intensity and composition) in connection with selecting CE voltages utilized for fragmentation at different points in time during an experiment. Larger ion masses are typically associated with longer peptide chains. In LC/MS, for example, low mass or short peptides tend to elute early during an experimental run while the larger mass or longer peptides tend to elute later in the run. In one embodiment, a same set of minimum and maximum values may be used for each EE scan resulting in the same ramped CE values for each EE scan. Alternatively, an embodiment may also vary the minimum and/or maximum values for each EE scan as needed during the course of an experiment since, with using a same set of such values for all EE scans, it may be that the minimum CE value selected is excessive for the smaller, more easily fragmented peptides eluting early in the experiment. Furthermore, use of only a single maximum value for all EE scans may be inadequate for efficient fragmentation of larger peptides eluting at later points in time during the experiment. In an embodiment in which the minimum and maximum CE values may vary with each EE scan, the minimum and maximum values selected for each EE may also vary as a function (linearly or otherwise) of lapsed time (elution time) of the experiment. Furthermore, in accordance with techniques herein, the minimum and maximum values for a single EE scan may be selected in accordance with criteria associated with the precursor ions being fragmented during the time of the EE scan. In other words, criteria associated with all precursor ions, or a portion thereof, eluting at a particular retention time may be used to determine the minimum and maximum CE values used for fragmentation.

Figure 3:
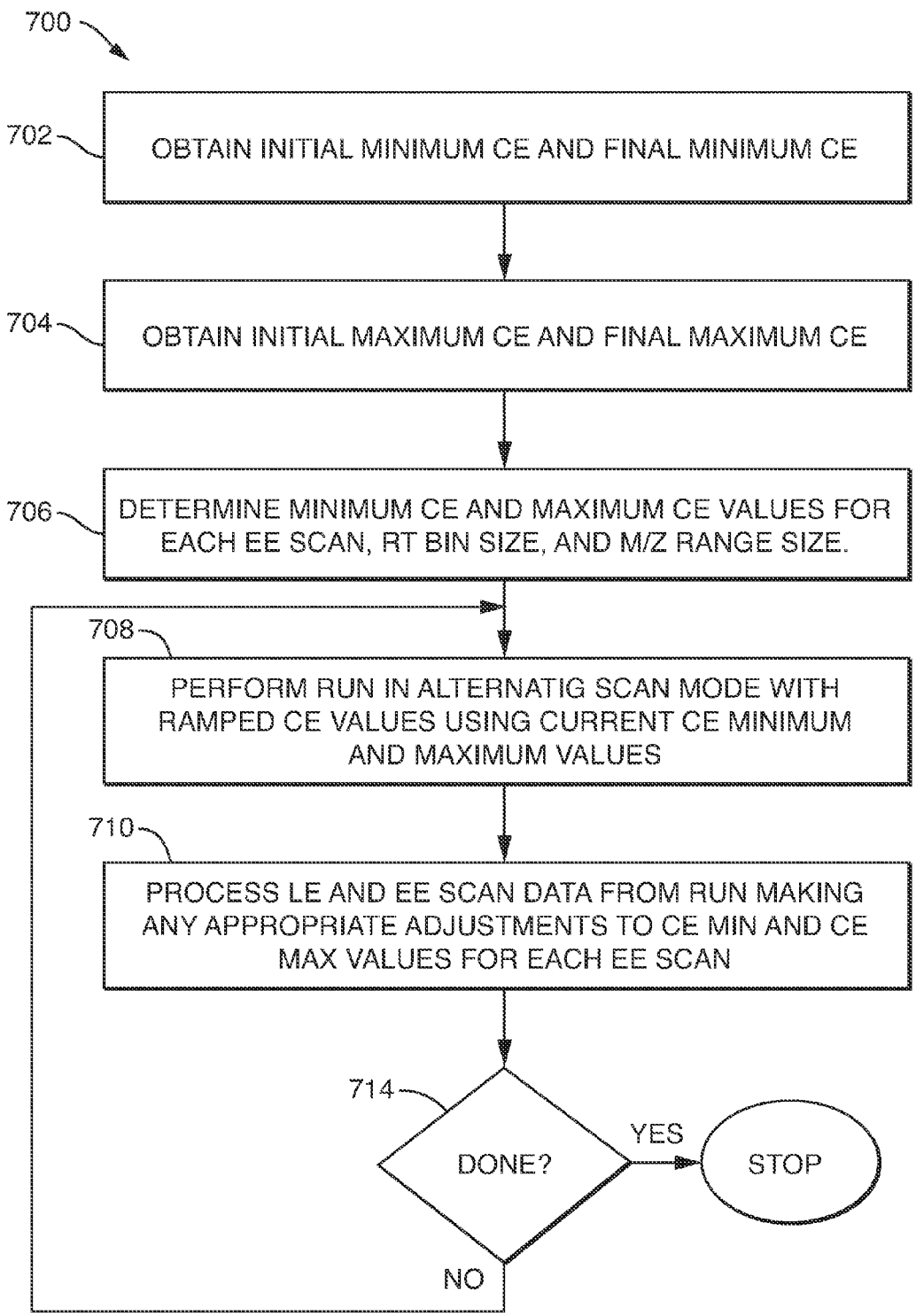
FIGS. 3 and 4 are flowcharts of processing steps that may be performed in an embodiment in accordance with techniques described herein.

Referring to FIG. 3, shown is a flowchart of processing steps that may be performed in an embodiment in accordance with techniques described herein for selecting CE voltages during fragmentation of precursor ions. In connection with processing of the flowchart 700, the modified version of the alternating scanning described in the Bateman '130 patent may be performed where alternating LE and EE scans are taken in sequence. In connection with the EE scan, the CE may be varied by increasing the CE from a minimum to a maximum CE value for the duration of the single EE scan. Values used for the minimum and maximum CEs for each EE scan may be determined in connection with processing described in following paragraphs. For example, as described in more detail below, CEs selected for a particular EE scan may be based on characteristics of eluting precursors which have associated fragment ions contained in the EE scan. Furthermore, processing of the flowchart 700 describes an embodiment of the techniques herein where the minimum and maximum CE values used for each EE scan may increase with the time at which the EE scan is performed. For example, the CE minimum for an EE scan performed at time N may be less than CE minimum for a subsequent EE scan performed at a time subsequent to N.

Figure 3B:
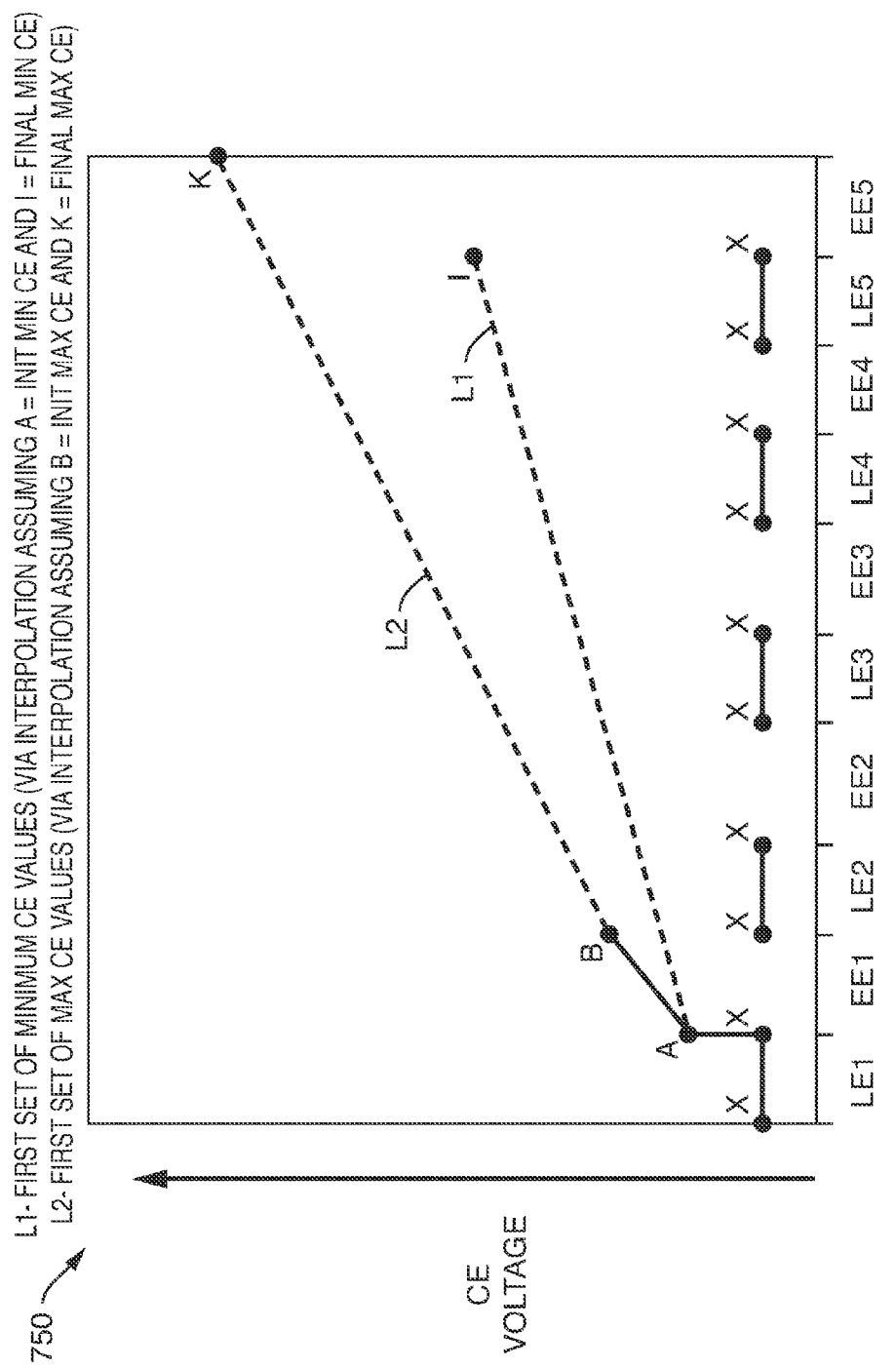
FIG. 3B is a graphical illustration of how initial minimum and maximum collision energy values may be determined for each EE (elevated energy) scan in accordance with an embodiment of the techniques herein.

At step 702, an initial minimum CE and final minimum CE are determined for the run or experiment. In other words, the initial minimum CE value is used as the minimum CE for the first EE scan and the final minimum CE value is used as the minimum CE for the last or final EE scan for the experiment. Other minimum CE values as used for other EE scans may be based on linearly interpolated values between the initial and final CE minimum values. The foregoing is illustrated with reference to FIG. 3B where, for example, point A may represent the initial minimum CE and point I may represent the final CE minimum value. Other minimum CE values for intermediate EE scans (between the first and last EE scan) may be determined based on linear interpolation using points A and I as endpoints. In FIG. 3B, it should be noted that LE scans for unfragmented or precursor ions are denoted LEn, where "n" is some integer (e.g., LE1, LE2, etc.). EE scans for fragmented ions are similarly denoted EEn. An LE scan having fragments in a corresponding EE scan is denoted by the corresponding integer (e.g., LEn includes precursors having fragments included in the scan data for EEn).

At step 704, an initial maximum CE and final maximum CE are determined for the run or experiment. In other words, the initial maximum CE value is used as the maximum CE for the first EE scan and the final maximum CE value is used as the maximum CE for the last or final EE scan for the experiment. Other maximum values as used for other EE scans may be based on linearly interpolated values between the initial and final CE maximum values as part of step 706 processing. The foregoing is illustrated with reference to FIG. 3B where, for example, point B may represent the initial maximum CE and point K may represent the final CE maximum value. Other maximum CE values for intermediate EE scans may be determined based on linear interpolation using points B and K as endpoints.

Techniques for performing linear interpolation are known in the art using the equation y=m*x+b, where x and y are coordinates of known points. Linear interpolation is one technique for curve fitting using linear polynomials and may be characterized as a simple form of interpolation. If the two known points, such as the initial minimum CE and the final minimum CE are given, respectively, by the coordinates ($x_0$, $y_0$) and ($x_1$,$y_1$), the linear interpolant is the straight line between these points. For a value x in the interval ($x_0$, $x_1$) the value y along the straight line is given from the equation $$\frac{y - y_0}{y_1 - y_0} = \frac{x - x_0}{x_1 - x_0}$$

Solving this equation for y, which is the unknown value at x, gives $$y = y_0 + (x - x_0)\frac{y_1 - y_0}{x_1 - x_0}$$

which is the formula for linear interpolation in the interval ($x_0$, $x_1$).

It should be noted that other forms of non-linear curve fitting techniques may also be used in an embodiment rather than using linear interpolation in order to determine other CE minimum and other CE maximum values for EE scans between the first and final EE scan of a run.

An embodiment may obtain the four values (initial minimum CE, final minimum CE, initial maximum CE, and final maximum CE) in a variety of different ways. One or more of the values may be user specified (such as input via a user interface or user data file), specified as default values (such as included inline in code or a configuration file), and the like. The values may be empirically determined, for example, based on results of previous experiments with the same sample where particular precursors are expected to elute during the course of the run. In one embodiment, the following exemplary values may be used: initial minimum CE=10 eV, final minimum CE=25 eV, initial maximum CE=25 eV, and final maximum CE=50 eV.

Step 706 processing also includes determining a retention time (RT) bin size and an m/z or mass range size used in connection with subsequent processing steps. In connection with the RT bin size selection, the entire elution time or duration time of the run is partitioned into intervals each of the specified RT bin size. For example, if an experiment will run for 100 minutes and an RT bin size of 2 minutes is selected, there will be 50 RT bins. As will be described in following paragraphs, LE scan data is used to determine the retention time and other information for precursor ions. The particular RT bin into which a precursor ion is placed is in accordance with the precursors' retention time. Precursor ions associated with each retention time may have different m/z or mass values and charge states. Use of the RT bin size and m/z or mass range size is illustrated in connection with subsequent examples.

At step 708, the run is performed using the modified alternating scan mode of the Bateman '130 patent where, when performing an EE scan, the CE voltage is ramped or increased for the duration of the EE scan. The CE voltage at a point in time during the single EE scan may also be determined by performing linear interpolation using the CE minimum and CE maximum of the EE scan as endpoints. With reference again to FIG. 3B for EE1, the CE during the scan EE1 is varied linearly between CE values represented by A and B. An embodiment may alternatively use other non-linear interpolation techniques to determine CE values for the duration of an EE scan.

After scan data is obtained as a result of step 708, the scan data may be processed at step 710 and any appropriate adjustments made to CE minimum and CE maximum values for each EE scan. Step 710 processing is described in more detail in connection with following figures and paragraphs. At step 714, a determination is made as to whether additional runs for a given sample are desired. If not, processing stops. If step 714 evaluates to yes, control proceeds to step 708 to generate a new set of scan data using the possibly revised CE values from step 710. Thus, in accordance with techniques herein, processing of the flowchart 700 may be performed for a number of iterations in order to make several possible adjustments to CE minimum and maximum values for use when fragmenting precursors. With each such iteration of steps 708 (in which another run is performed) and step 710, the CE values used in connection with fragmentation may be further refined or improved. The CE values determined with the last such iteration may be used in connection with processing the same sample at a later point in time or when processing samples containing the same peptides and/or proteins. The resulting LE and EE scan data associated with the last such iteration may be used to identify proteins in the sample such as, for example, using the techniques described in PCT Publication No. WO2007/140251, published Dec. 6, 2007 (PCT application no. PCT/US07/069,657, international filing date May 24, 2007), APPARATUS AND METHOD FOR PERFORMING MASS SPECTROSCOPY, Geromanos et al., which is incorporated by reference herein. The foregoing is just one further use of the techniques herein.

Figure 4:
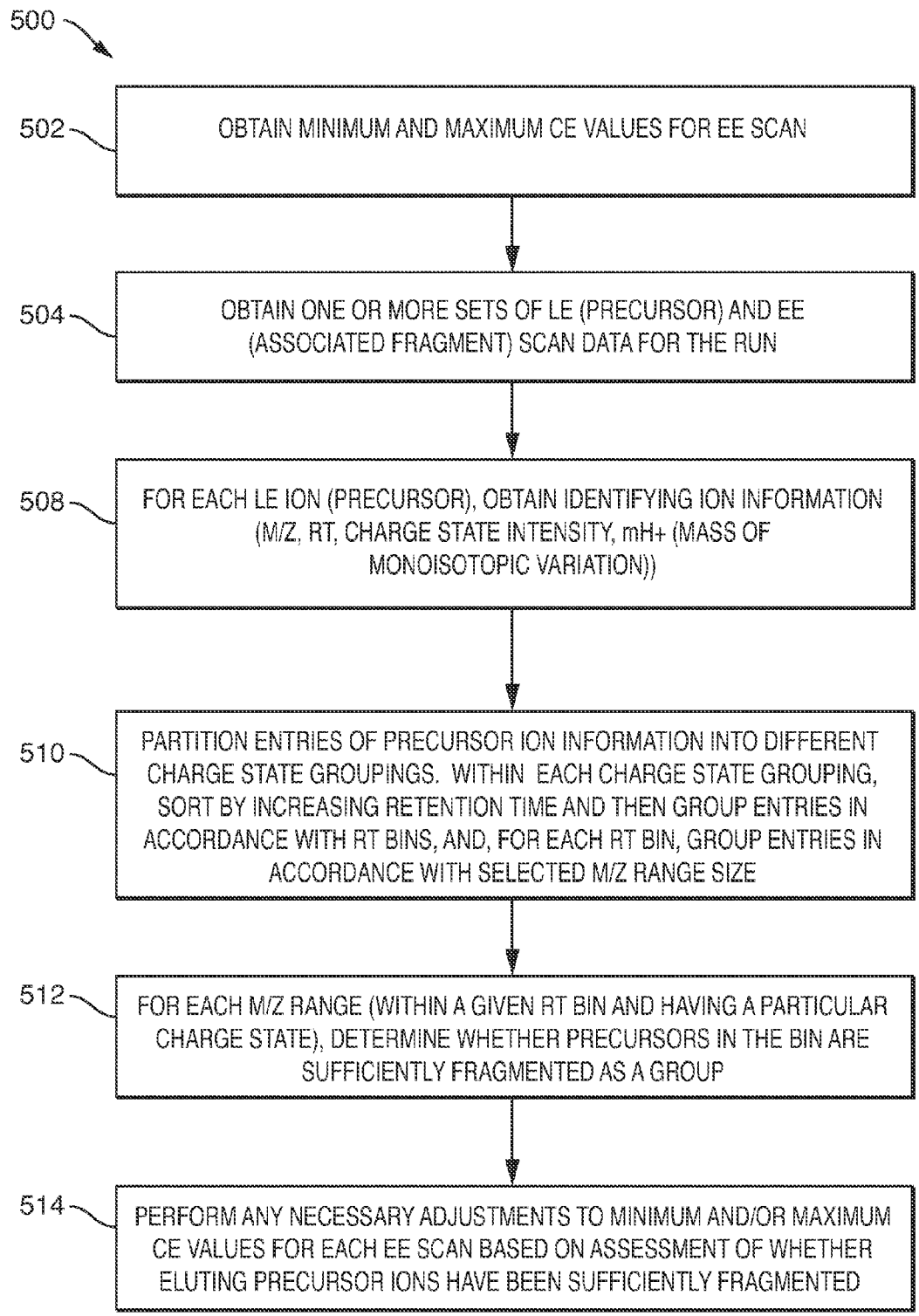

Referring to FIG. 4, shown is a flowchart of processing steps 500 that may be performed in an embodiment in connection with processing scan data from a run as may be produced from step 708 processing of FIG. 3. The steps of the flowchart 500 provide more detail of processing step 710 from FIG. 3. At step 502, the current minimum CE and maximum CE values for all EE scans may be obtained. The data obtained in step 502 may be modified in a subsequent step 514 described below. At step 504, the one or more sets of LE and corresponding EE scan data for the run are obtained. At step 508, for each precursor ion in each LE scan, the precursor's LE scan data is processed to obtain identifying ion information such as the precursor ion's m/z, retention time, charge state, intensity, and mH+ (mass of monoisotopic variation). The foregoing information may also be more generally referred to as characteristics of an ion and may be obtained for each precursor by processing the LE scan data using the techniques described in PCT Publication No. WO2007/140327 as mentioned above. As a result of performing the processing of step 508, a row or entry containing the information may be obtained for each charge state of a precursor occurring in all acquired LE scan data, where, each of the different charge states for a same precursor has the same monoistopic variation (e.g., same mH+ for the $C^{12}$ (Carbon-12) ion). At step 510, the entries of precursor ion information may be partitioned into different charge state groupings. Within each charge state grouping, the entries may then be sorted by increasing retention time and grouped in accordance with the RT bins. For each RT bin, entries in the RT bin may be sorted in accordance with increasing mass or m/z values. The following may be representative of how the entries of precursor ion information may be ordered and grouped after performing step 510.

| CS (charge state) | RT | m/z | intensity (representing the sum intensity) |
|---|---|---|---|
| 1 | 1 | 500 | 1215 |
| 1 | 1 | 503 | 2541 |
| 1 | 1 | 600 | 10215 |
| 1 | 2 | 155 | 25145 |
| 1 | 2 | 180 | 4875 |
| . | . | . | |
| . | . | . | |
| . | . | . | |
| 2 | 1 | 308 | 251 |
| 2 | 1 | 309 | 368 |
| 2 | 2 | 180 | 31542 |
| . | . | . | |
| . | . | . | |
| . | . | . | |
| 3 | 1 | 500 | 6547 |
| 3 | 2 | 850 | 685741 |

It should be noted that the foregoing precursor ion information is merely exemplary. The intensity included in the foregoing precursor ion information may represent the sum intensity for the precursor ion.

Figure 7:
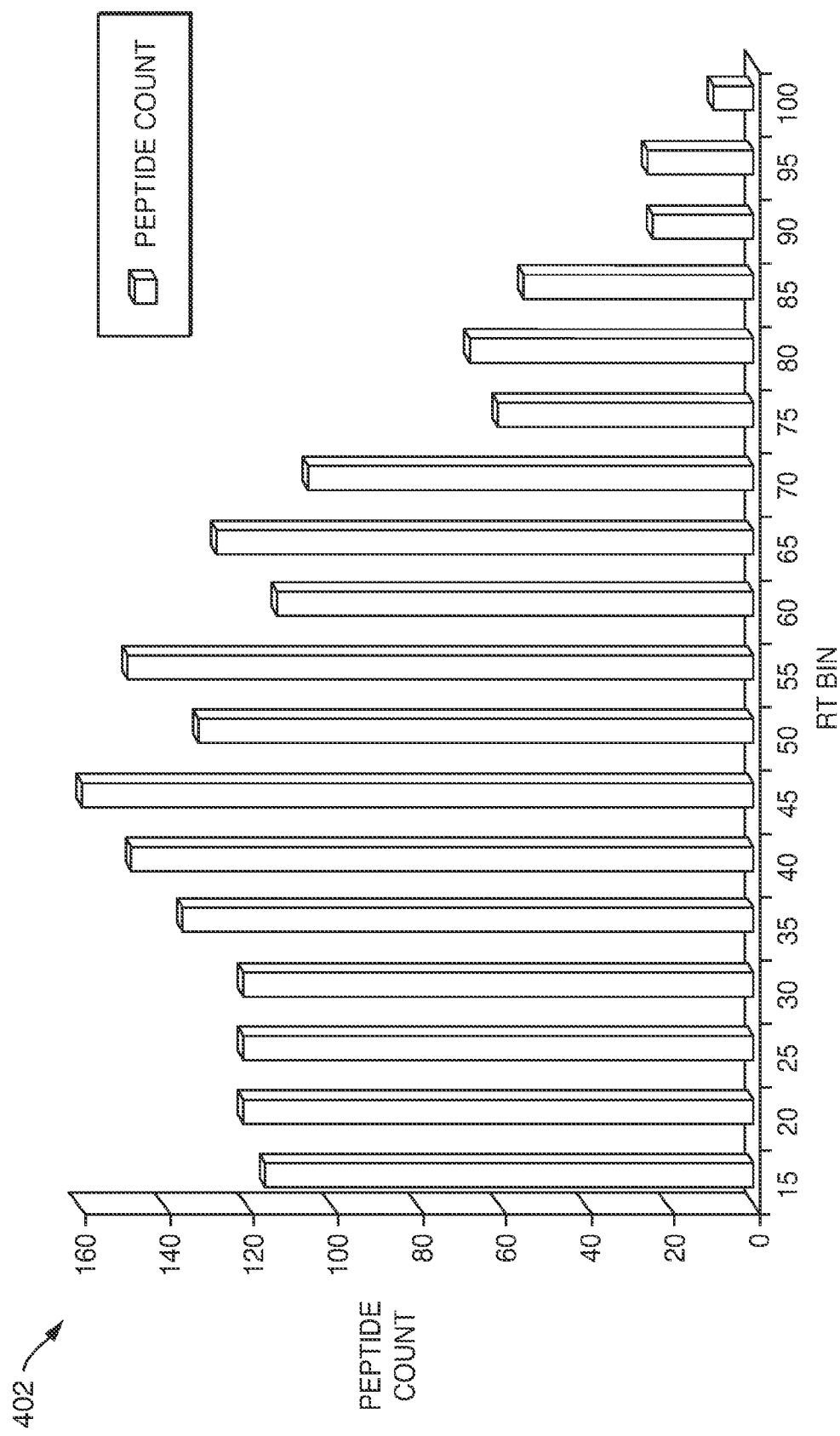
FIG. 7 is an example illustrating a precursor peptide count distribution for defined retention time bins.

Referring to FIGS. 5A, 5B and 6, shown are examples of tables collectively representing how the individual entries may be grouped in accordance with a precursor's charge state, retention time and m/z where the RT bin size=5 and the m/z range=100. FIG. 5A includes a table 300 of precursors having a charge state=1 and FIG. 5B includes a table 350 of precursors having a charge state=2. FIG. 6 includes a table 400 of precursors having charge state=3. Each entry in the table represents a number of precursors having the associated charge state and also falling into the indicated retention time bin and m/z range. FIG. 7 is another graphical illustration of the same data set used to generated tables of FIGS. 5A, 5B and 6. FIG. 7 graphically illustrates a distribution of the total number of peptide precursors falling into each 5 minute RT bins. Each precursor contributing to a count maintained in one of the entries of tables 300, 350 or 400 may be identified using a tuple corresponding to the table entry:

(charge state, RT bin, m/z range)

Figure 7A:
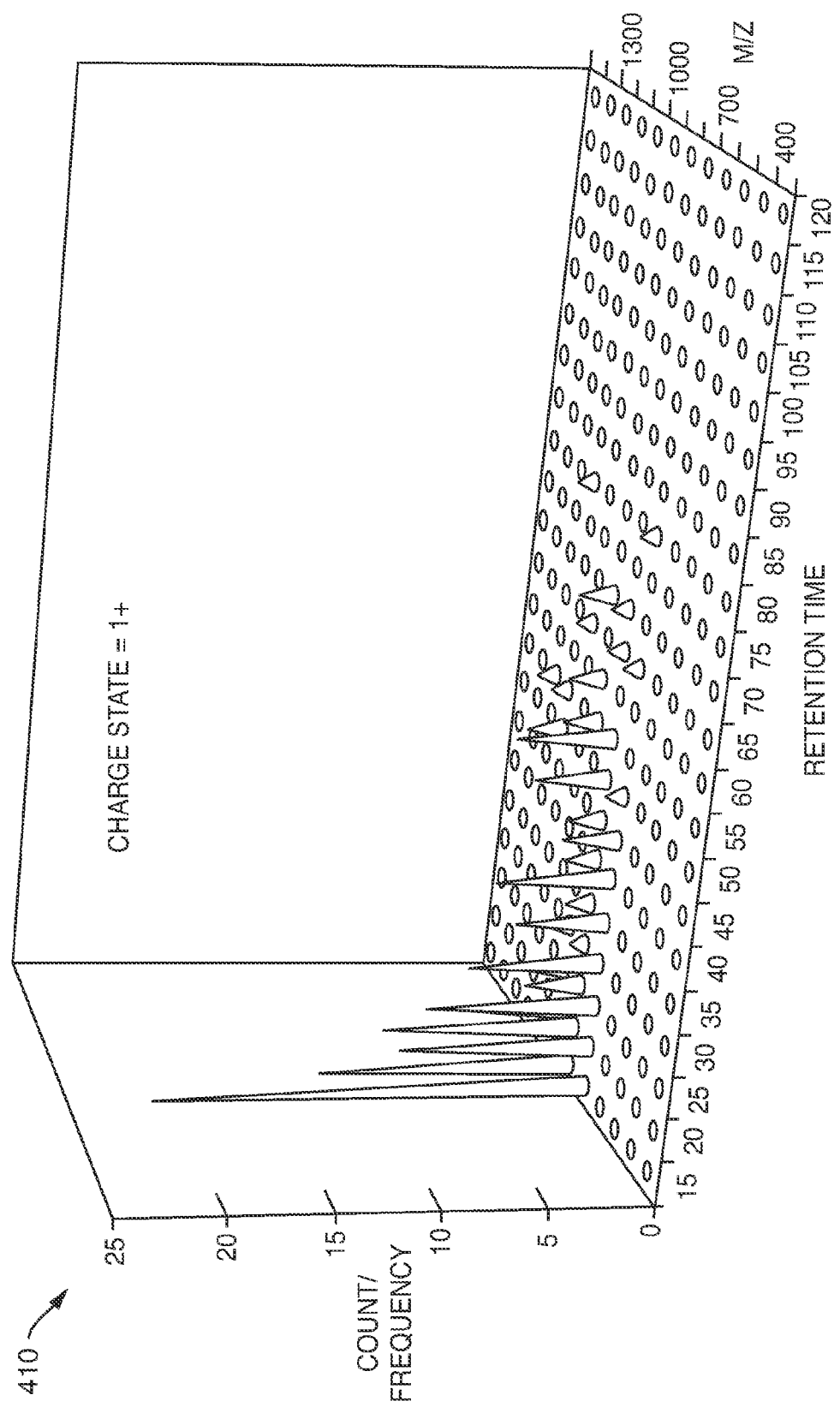
FIGS. 7A, 7B and 7C are examples graphically illustrating ion frequency occurrences for different charge states for the data tables from FIGS. 5A, 5B and 6.

Referring to FIG. 7A, shown is an example of a graphical illustration of frequency or count of the number of precursors having a charge state=+1.

Figure 7B:
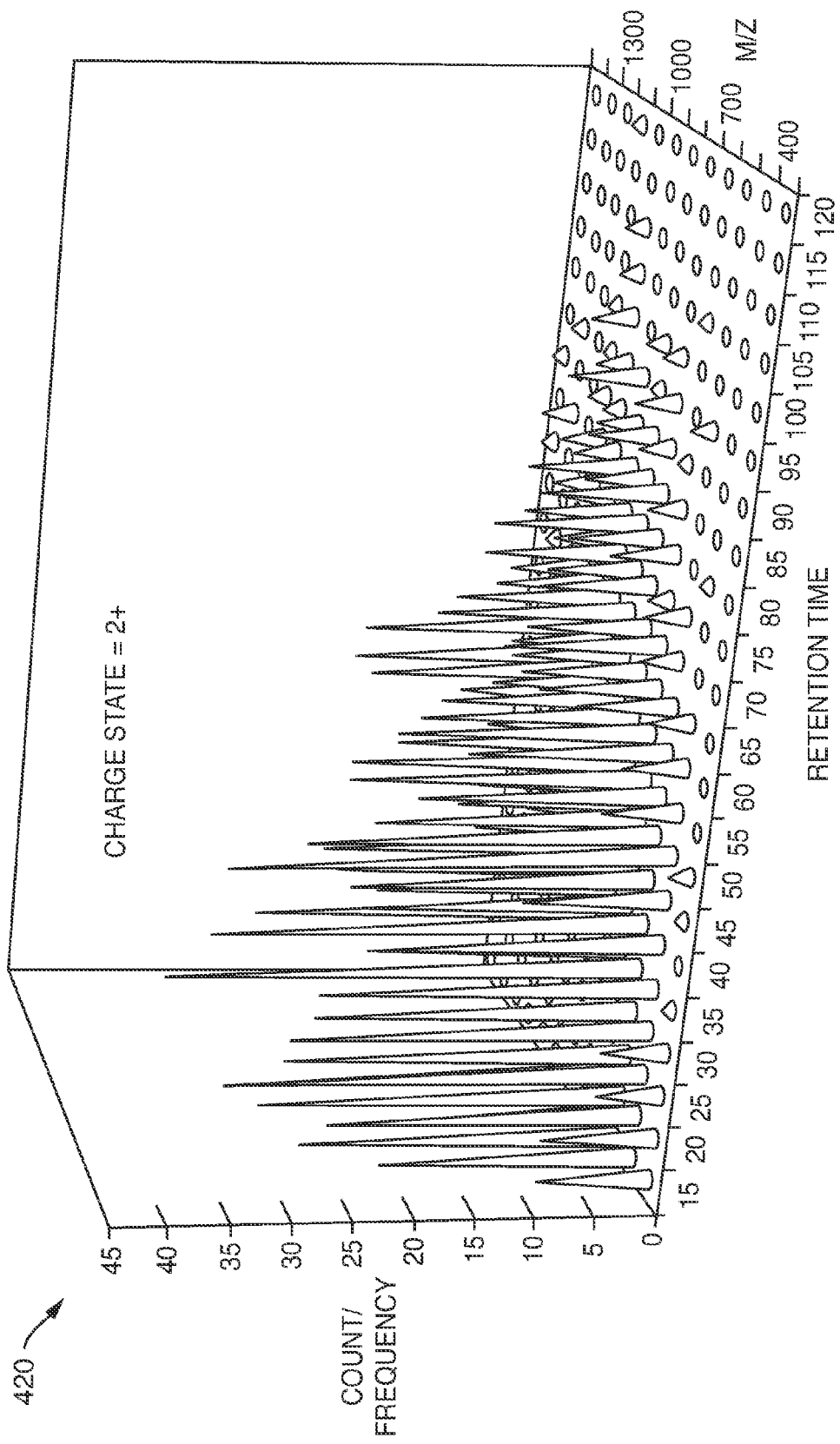

Referring to FIG. 7B, shown is an example of a graphical illustration of frequency or count of the number of precursors having a charge state=+2.

Figure 7C:
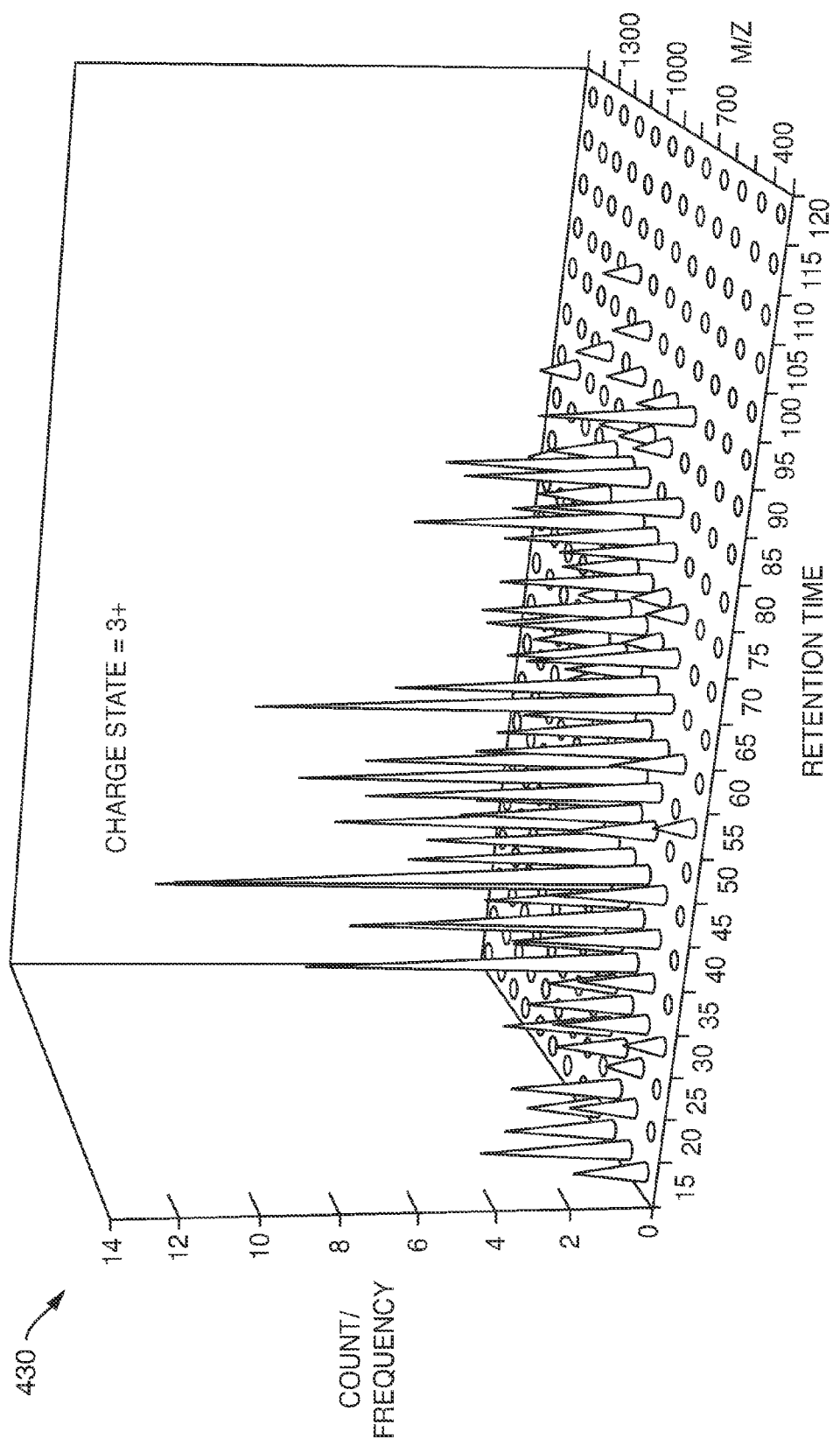

Referring to FIG. 7C, shown is an example of a graphical illustration of frequency or count of the number of precursors having a charge state=+3.

The examples of FIGS. 7A, 7B and 7C provide illustrations of the data used to produce FIGS. 5A, 5B, 6, and 7. With reference to the foregoing FIGS. 7A, 7B and 7C, note the tendency of higher charge states to increase with retention time. The frequency of ions having a higher charge state tends to increase with retention time. With reference to FIG. 7A, it should be noted that the ions having the lowest charge state=+1 tend to appear with high frequency at earlier retention times and tend to decrease in frequency at later retention times. In contrast, for example with reference to FIG. 7C, it should be noted that ions having the highest charge state examined in this illustration=+3 tend to appear with greater frequency at later retention times.

With reference back to FIG. 4 at step 512, the LE and EE scan data may be examined to determine which precursors have been sufficiently fragmented. As indicated in step 512, an embodiment may perform such an assessment for each m/z grouping of precursors. In other words, groups of precursors are examined as denoted in connection with the tables of FIGS. 5A, 5B and 6 so that all precursors falling within an m/z range within a given RT bin and having a particular charge state (e.g., identified using the same tuple) may be assessed as a unit. For each such m/z grouping, it is determined whether as a whole, all in the m/z grouping have been sufficiently fragmented. An embodiment may perform such an assessment for each m/z grouping or based on other partitioning in a variety of different ways. Techniques that may be used in an embodiment in connection with step 512 processing to determine whether there has been sufficient fragmentation with respect to individual precursors and groups of precursors are described below. At step 514, any necessary adjustments are made to the minimum and/or maximum CE values for each EE scan based on the assessment in step 512 as to whether the eluting precursor ions of the corresponding LE scan have been sufficiently fragmented.

Figure 8A:
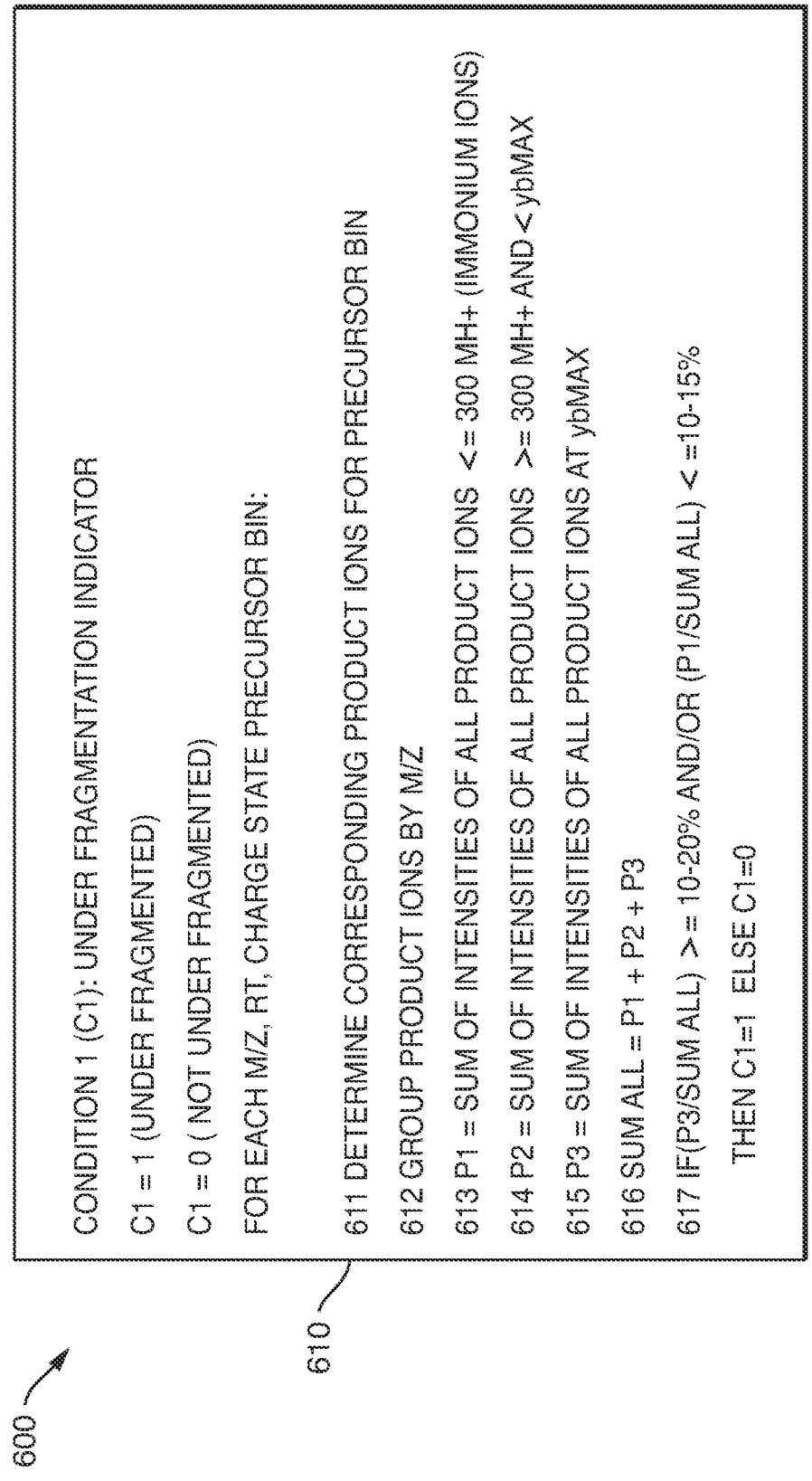
FIGS. 8A and 8B are examples describing indicator values that may be determined in an embodiment for use in determining whether a precursor has been sufficiently fragmented.
Figure 8B:
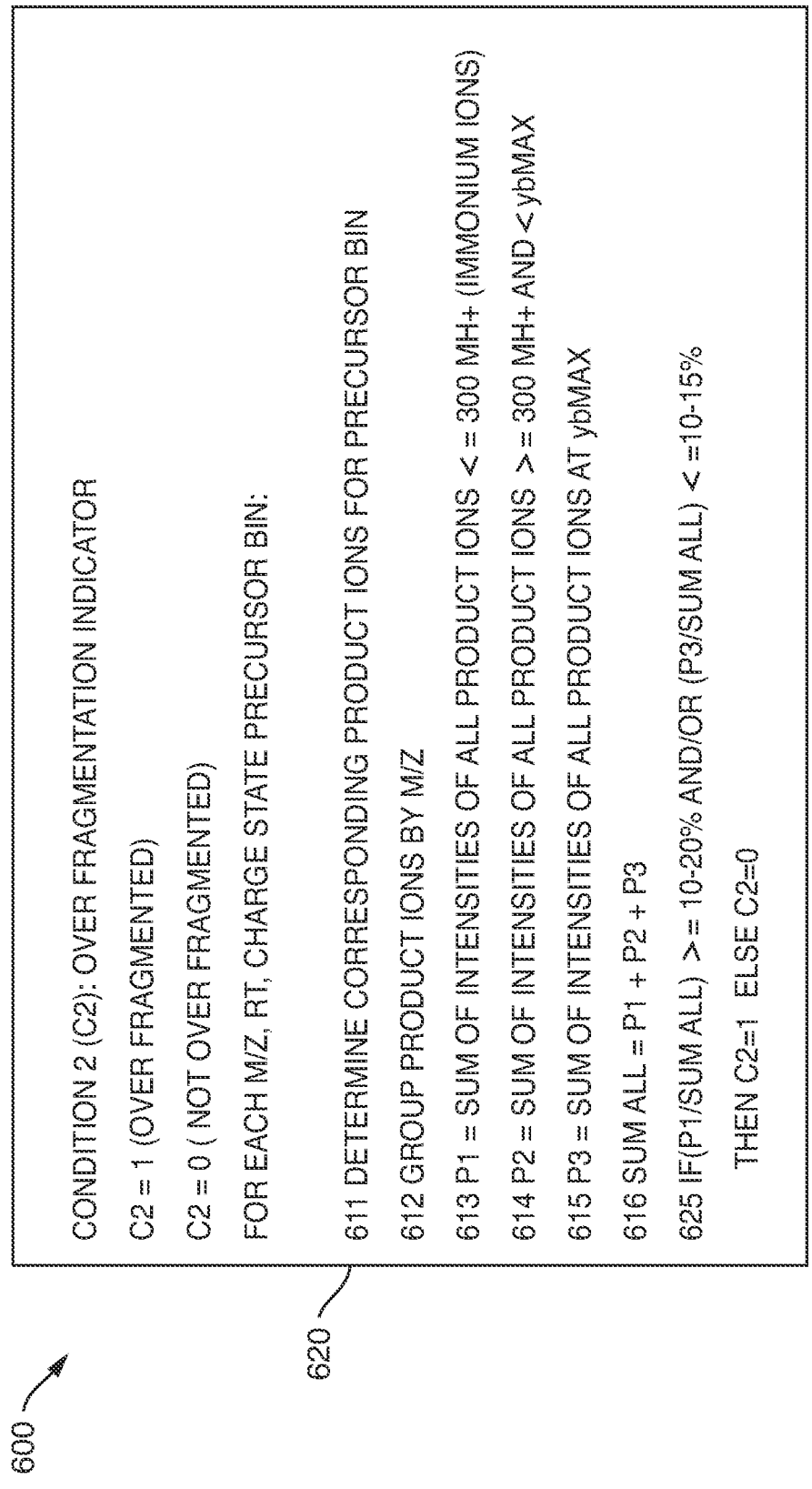

In one embodiment, each precursor may be evaluated in accordance with two conditions as illustrated in FIGS. 8A and 8B where a first condition C1 is referred to as an under fragmentation indicator and a second condition C2 is referred to as an over fragmentation indicator. Processing may be performed by executing code to determine a value for C1 and C2 with respect to each bin of precursors in the LE scan using the ion information acquired as described above. Element 610 describes processing that may be performed in order to determine a value for the C1 indicator for a particular bin (defined by a charge state, RT bin, m/z range) so that C1 has a value=1 if it is determined that the precursors therein have been under fragmented, and a value of 0 otherwise.

In connection with performing processing of FIGS. 8A and 8B for determining values of both C1 and C2, an embodiment in accordance with techniques herein may make a simplifying assumption to determine which EE scan data for fragments or product ions is attributable to (associated with) a particular precursor in the LE scan. If a product ion has approximately the same retention time (e.g., same retention time within some given time window for error) as a precursor, the product ion is determined to be associated with that particular precursor (e.g., the product ion has been produced as a result of fragmentation of the precursor having the same retention time).

Prior to performing processing of FIGS. 8A and 8B, the EE scan data may be processed as described in PCT Publication No. WO2007/140327 to obtain a list of m/z and retention time values for each fragment ion. It should be noted that the mass that may be used in connection with FIGS. 8A and 8B processing may be the mass of MH+ for the monoistopic variation of an ion as may be determined from a particular m/z as:

(m/z*charge state)−((charge state−1)*1.0007825)

It should be noted that if there is a fragment ion in the EE scan data having the same mass, such as MH+, and retention time as that of the precursor included in the LE scan, then the precursor (unfragmented) is included in the EE scan.

Referring to element 610, processing will now be described which may be performed for each retention time bin of precursors (precursors in a retention time bin, for a given charge state and m/z range). At step 611, the corresponding product ions from the EE scan data are determined with respect to all precursors in the current precursor bin. In other words, step 611 determines which product ions are fragments of the precursors in the current precursor bin being processed. As described elsewhere herein, the EE scan data may be processed to determine fragment ion retention times. Those fragments having the same retention times as the precursors in the current bin are determined as fragments associated with the precursors in the current bin. At step 612, the product ions determined in step 611 may be grouped by m/z. At step 613, P1 may be determined as the sum of intensities of all product ions from step 611 which are <=300 MH+ (e.g., an immonium ion). As indicated in step 613 of element 610, the sum intensity of the immonium ions present in the EE scan having a same retention time as the precursor ion are determined. As described above, the EE scan data may be processed in accordance with techniques of PCT Publication No. WO2007/140327 to obtain a list of masses and retention time values for the product ions. This list of product ions having a same retention time as that of the precursor may be searched against a predetermined list of 20 amino acids comprising the immonium ions. More specifically, the mH+ (mass) of each fragment having a same retention time as the precursor may be compared to a mass for each amino acid in the predetermined list. If there is a match, then the fragment is determined to be an immonium ion. Step 613 adds the intensities of all such fragments from the EE scan determined to be an immonium ion. It should be noted that the intensities utilized may represent a sum of intensities over the different charge states for the same product ion. Step 614 determines P2 as the sum of intensities of all product ions having an MH+ which is greater than 300 MH+ (not an immonium ion) and which is less than a ybMAX for a residual precursor. In other words, for a given bin, there may be one or more ybMAX values corresponding to the one or more precursors in the bin. For a product ion in an EE scan having a first retention time, its corresponding ybMAX is that MH+ for the precursor having the same first retention time as the product ion. In step 615, P3 is determined as the sum of intensities of all product ions at ybMAX. P3 represents the sum of intensities of all unfragmented or intact precursors in the EE scan data. Step 616 determines a sum, denoted SUM ALL, of P1+P2+P3, wherein P1, P2 and P3 are as calculated, respectively, in steps 613, 614 and 615. At step 617, a first determination is made as to whether the ratio of (P3/SUM ALL) is greater than or equal to a first threshold percentage. For example, the first threshold percentable may be selected from the inclusive range of 10-20%. Additionally, step 617 performs a second determination as to whether the ratio of (P1/SUM ALL) is less than or equal to a second threshold percentage. For example, the second threshold percentage may be selected from the inclusive range of 10-15%. An embodiment may determine a final logical result of the IF condition of step 617 by logically ANDing the results of the foregoing first determination and second determination. Alternatively, an embodiment may determine a final logical result of the IF condition of step 617 by logically ORing the results of the foregoing first determination and second determination. In step 617, if the final logical result of the IF condition evaluates to true then C1=1 indicating that the precursor is under fragmented. If the IF condition in step 617 evaluates to false, then C1=0 indicating that the precursor is not under fragmented.

Element 620 describes processing that may be performed in order to determine a value for the C2 indicator so that C2 has a value=1 if it is determined that the precursor has been over fragmented, and a value of 0 otherwise. As indicated in element 620, processing steps 611, 612, 613, 614, 615 and 616 may be performed as described above in connection with element 610. At step 625, a first determination is made as to whether the ratio of (P1/SUM ALL) is greater than or equal to a first threshold percentage. For example, the first threshold percentable may be selected from the inclusive range of 10-20%. Additionally, step 625 performs a second determination as to whether the ratio of (P3/SUM ALL) is less than or equal to a second threshold percentage. For example, the second threshold percentage may be selected from the inclusive range of 10-15%. An embodiment may determine a final logical result of the IF condition of step 625 by logically ANDing the results of the foregoing first determination and second determination. Alternatively, an embodiment may determine a final logical result of the IF condition of step 625 by logically ORing the results of the foregoing first determination and second determination. In step 625, if the final logical result of the IF condition evaluates to true then C2=1 indicating that the precursor is over fragmented. If the IF condition in step 625 evaluates to false, then C2=0 indicating that the precursor is not over fragmented.

It should be noted that the foregoing thresholds and/or ranges used in accordance with techniques herein are exemplary with respect to determining over and/or under fragmentation. For example, an embodiment in accordance with techniques herein may determine a desired optimal fragmentation state through analysis of the EE scan data as one where the immonium ion percentage (e.g., P1/SUM ALL) is less than 10% and the percentage of intact or residual precursors (e.g., P3/SUM ALL) is less than 15%. The embodiment may select threshold percentages for use in determining under and/or over fragmenting based on a window or range of acceptable percentages in accordance with the foregoing desired fragmentation state.

The foregoing indicators C1 and C2 indicate, respectively, whether there has been under or over fragmentation in each m/z, RT, charge-state bin. Indicators such as C1 and C2 as well as other information used in an embodiment to determine whether, on average, the precursors in any m/z, RT charge-state bin have been sufficiently fragmented may also be referred to more generally as fragmentation criteria. Information regarding over and/or under fragmentation for individual m/z, rt charge-state bins may be combined in a variety of different ways to determine collectively whether all bins at a particular retention-time (regardless of m/z and charge-state) have been sufficiently fragmented. In one embodiment, the foregoing indicators C1 and C2 may be examined for a group of precursors to determine whether all such precursors at a particular retention time (or within a particular retention time range) are sufficiently fragmented. Ideally, all values for C1 and C2 may be 0.

What will now be described is one way in which an embodiment in accordance with techniques herein may combine C1 and C2 values associated with multiple m/z, rt charge-state bin with respect to a single retention time. Following for purposes of illustration is a simplified first set of data as may be associated with a single RT=35 including data across different charge states and m/z values. In the following, CS is charge state, RT is retention time, Int is intensity or sum of intensities for all precursors represented by the corresponding row, % Int is the percentage of intensity (relative to sum of intensity values in Int columns), C1 is the value of condition indicator C1 described herein, C2 is the value of condition indicator C2 described herein. A row of data in the following table may correspond to data of a particular (m/z, RT=35, charge-state) bin for which C1 and C2 may be determined as described above. In the following tables, CS1 refers to charge state=1, CS2 refers to charge state=2, CS3 refers to charge state=3 for one or more ions in a given RT bin.

TABLE 1

| Name | MH+ | m/z | Int | CS | RT | % Int | C1 | C2 | VALA = (C1 + C2) * % Int |
|---|---|---|---|---|---|---|---|---|---|
| CS1 | 1200 | 1200 | 6000 | 1 | 35 | 7.6 | 0 | 1 | 7.6 |
| CS2 | 1250 | 625 | 60000 | 2 | 35 | 77.0 | 0 | 0 | 0 |
| CS3 | 1260 | 420 | 12000 | 3 | 35 | 15.4 | 0 | 1 | 15.4 |
| | | | | | | | | | 23.0 If value <25% no-change |

Additionally, for the above first set of data of TABLE 1, a FINAL SUM may be determined which is the sum of VAL A for each row. For example, FINAL SUM based on the above TABLE 1 data is 23.0 determined as a sum of the values: 7.6, 0, and 15.4 for each row. Additionally, a sum of C2 and C1 values for the RT=35 may be determined. The variable SUM_C2 may represent the sum of the C2 column above which has a value of 2. The variable SUM_C1 may represent the sum of the C1 column above which has a value of 0. It should be noted that VAL_A for each row in the table may be characterized as representing a weighted value where the determination of under and/or overfragmentation based on C1 and C2 may be weighted in accordance with the % Int for that row.

In one embodiment, if the foregoing FINAL_SUM<25%, it may be determined that there is sufficient fragmentation and therefore no change is made to either the minimum CE or the maximum CE for the EE scan associated with the RT=35. However, as will be further illustrated in connection with other exemplary sets of data, if FINAL_SUM is equal to or greater than 25%, an adjustment to the minimum CE and/or maximum CE may be made. The extent to which any adjustment to CE is made may vary in accordance with SUM_C2 and/or SUM_C1.

Consider the following second set of data:

TABLE 2

| Name | MH+ | m/z | Int | CS | RT | % Int | C1 | C2 | VALA = (C1 + C2) * % Int |
|---|---|---|---|---|---|---|---|---|---|
| CS1 | 1200 | 1200 | 6000 | 1 | 35 | 7.6 | 0 | 1 | 7.6 |
| CS2 | 1250 | 625 | 40000 | 2 | 35 | 51.0 | 0 | 0 | 0 |
| CS3 | 1260 | 420 | 32000 | 3 | 35 | 41.4 | 0 | 1 | 41.4 |
| | | | | | | | SUM C1 = 0 | SUM C2 = 2 | 49 If value >25% change |

Based on the foregoing, FINAL_SUM=49%, SUM_C2=2, and SUM_C1=0. Since FINAL_SUM>25%, it may be determined that an adjustment to the EE scan minimum CE and/or maximum CE is performed. Following is a first logical representation of how an embodiment in accordance with techniques herein may adjust the maximum CE for the EE scan associated with RT=35 based on the data of TABLE 2 above:
if (FINAL_SUM>25%) then
   if SUM_C2=1 then decrease maximum CE for EE scan by 20%
   else decrease maximum CE for EE scan by 40%
if (FINAL_SUM>25%) then
   if SUM_C1=1 then increase maximum CE for EE scan by 20%
   else increase maximum CE for EE scan by 40%

Based on TABLE 2 data and the above logical representation, the precursors associated with RT=35 are being overfragmented and the maximum CE may be decreased by 40% It should be noted that the values of 20% and 40% are exemplary and an embodiment in accordance with techniques herein may choose to adjust in different increments and/or decrements.

An embodiment may similarly adjust the minimum CE value for an EE scan. For example, an embodiment may make adjustments to the minimum CE rather than the maximum CE as described above so that the adjustment determination used may be represented in the following second logical representation as:

if (FINAL_SUM>25%) then
    if SUM_C2=1 then decrease minimum CE for EE scan by 20%
        else decrease minimum CE for EE scan by 40%
if (FINAL_SUM>25%) then
    if SUM_C1=1 then increase minimum CE for EE scan by 20%
        else increase minimum CE for EE scan by 40%

An embodiment may first select to adjust either the minimum CE or the maximum CE and then re-evaluate the results prior to making further adjustments to the CE. Alternatively, an embodiment may also select to make adjustments to both the minimum CE and maximum CE and then re-evaluate the results prior to making further adjustments. For example, rather than adjust either only the minimum CE or only the maximum CE as described above, an embodiment may adjust both the minimum CE and the maximum CE for a single EE scan and then re-evaluate the results. In this latter instance, the embodiment may adjust both the minimum CE and the maximum CE so that the sum of the adjustments is equal to 20%, 40%, and the like, as represented by the following third logical representation:

if (FINAL_SUM>25%) then
    if SUM_C2=1 then decrease minimum CE by 10% and 2 decrease maximum CE by 10%
        else decrease minimum CE by 20% and
        decrease maximum CE by 20%
if (FINAL_SUM>25%) then
    if SUM_C1=1 then increase minimum CE by 10% and increase maximum CE by 10%
        else increase minimum CE by 20% and
        increase maximum CE by 20%

More generally, whether an embodiment makes adjustments to the minimum CE value and/or a maximum CE value for a given EE scan (as well as an amount of any such adjustment) may be proportional to the degree of over- or under-fragmentation. In one embodiment in accordance with techniques herein, if a high degree of over-fragmentation is determined, the minimum CE value may be adjusted (e.g., decreased) first prior to making an appropriate adjustment (e.g., decrease) to the maximum CE value.

As a further example, consider the following third set of exemplary data in determining the intensities. It should be noted that the sum intensity values used may represent normalized sum intensity values based on the count or frequency such as illustrated in FIGS. 7A-C. The normalization may be based on the median normalized sum intensity of ions at a given charge state, mass, and retention time. First as illustrated in FIGS. 7A-C the number of ions illustrating a given charge-state and m/z are counted in each retention-time bin. In addition the sum intensity of all charge-state ions in each retention-time bin is calculated as well as the sum intensity by charge-state. The summed calculated intensity values for each charge-state group are then normalized to the ion count or frequency for that group. A ratio is calculated by dividing the normalized sum intensities by charge-state group by the sum intensity of all charge-state groups.

Following are further variations and examples of how the C1 and C2 values may be used collectively for a given RT bin (including all m/z and charge states) to determine whether there has been sufficient fragmentation (e.g., over or under fragmentation) and whether there should be any adjustments made with respect to collision energy for EE scans associated with the RT bin.

In one embodiment, the total (sum) number of occurrences of C1=0 and C2=0 may be determined for each RT bin (e.g., such as for each 2 minute RT bin across all m/z values and charges states at RT=2). As noted above, when both C1 and C2 are 0, it represents a determination of sufficient fragmentation in that neither over nor under fragmentation is determined. For each RT bin, if the total of such cases where C1=0 and C2=0 is above a threshold number or amount (e.g. as a percentage, such as 50%, of all precursors in the RT bin), an embodiment may determine that no adjustments to CEs for EE scans occurring during the RT bin are needed.

In another embodiment, the total (sum) number of occurrences of C1=1 and C2=1 may be determined for each RT bin. In a similar manner to that as described above, the total number of occurrences for each of the cases (e.g., C1=0, C2=1) and (C1=1, C2=0) may also be determined and used to evaluate, respectively, whether there has been under fragmentation and/or over fragmentation within a particular RT bin.

Figure 9:
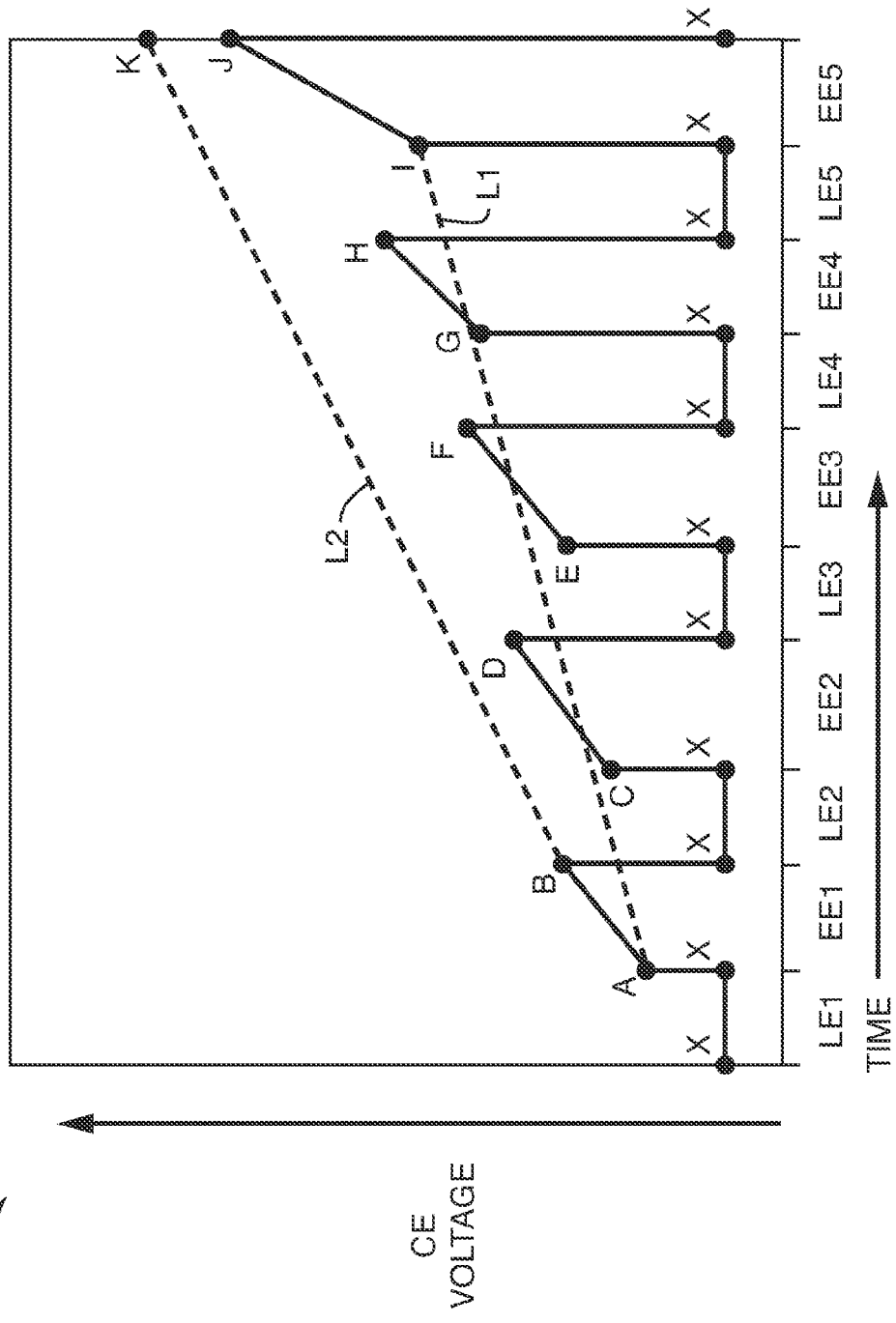
FIG. 9 is a graphical illustration of collision energy values that may be determined in an embodiment in accordance with techniques described herein.

Referring to FIG. 9, shown is an example graphically illustrating CE voltages as may be determined using the techniques herein. As described above, the CE voltages illustrated may be used with the alternating LE-EE scanning technique of the Bateman '130 patent with the modification to vary the CE during the EE scan. The example 800 illustrates the CE

TABLE 3

|  | MH+ | m/z | Int | CS | RT | % Int | C1 | C2 | VALA = (C1 + C2) * % Int |
|---|---|---|---|---|---|---|---|---|---|
| CS1 | 1200 | 1200 | 6000 | 1 | 35 | 7.6 | 0 | 0 | 0 |
| CS2 | 1250 | 625 | 40000 | 2 | 35 | 51.0 | 0 | 1 | 51 |
| CS3 | 1260 | 420 | 32000 | 3 | 35 | 41.4 | 0 | 1 | If value (41.4) >25% CS3 = 1 |
| Sum |  |  |  |  |  |  | SUM_C1 = 0 | SUM_C2 = 2 | 92.4 If value >25% change |

Based on the above TABLE 3 data, the FINAL_SUM=92.4%, SUM_C1=0 and SUM_C2=2 so that the processing performed by the first logical representation above for adjusting the maximum CE may determine that precursors as a whole for the RT=30 are being overfragmented and the maximum CE may be decreased by 40%.

In connection with the foregoing exemplary data sets in above TABLEs, the following should be noted with respect to minimum and maximum values for each EE scan as may be determined after one or more runs resulting in modification and adjustment of the CE minimum and maximum values. FIG. 9 represents the ending CE values generated from starting CE values as previously described in FIG. 3B. In the example 800, X denotes the CE for the LE scan. The following points denote the CE minimum and maximum values for each EE scan:

| CE minimum | CE maximum | EE scan # |
|---|---|---|
| A | B | 1 |
| C | D | 2 |
| E | F | 3 |
| G | H | 4 |
| I | J | 5 |

CE values during each EE scan may be varied by increasing the CE value linearly from the CE minimum to the CE maximum for the EE scan. As described above, the dashed line L1 denotes the first or starting set of minimum CE values and the dashed line L2 denotes the first or starting set of maximum CE values.

In accordance with techniques herein described above, a first set of CE values may be selected and used with a sample during a first run. The mass spectra data from the first run may be evaluated as described above and then the CE values used in connection with fragmentation of precursors in elevated energy scans may be accordingly adjusted and the adjusted CE values used in a second run. Thus, the techniques herein may be applied in an iterative manner so that the CE values used for fragmentation are tuned for use with different samples, as well as other changes made to apparatus used in conducting the experiment.

Although reference in illustrative examples herein may be made to applications using protein digests analyzed using the modified version of the alternating EE-LE scanning technique described in the '130 Bateman patent, an embodiment may use the techniques herein in connection with selection of a collision energy for use with other methodologies known in the art such as, for example, data dependent analysis or acquisition (DDA) used to isolate selected precursor ions and identify product ions for the selected isolated precursor. In one embodiment, a mass spectrometer may be used to perform DDA in which the mass spectrometer includes a collision cell and a quadrupole. When operating in accordance with the DDA technique in one possible embodiment, the quadrupole may be used as a filter in a first phase to selectively isolate and select only precursors of interest. Thus, only selected precursors are produced as an output of the first filtering phase. The selected precursors are then passed to a collision cell where they are fragmented, as using a sufficiently high voltage, to generate fragments or product ions and obtain a desired number of scans for the isolated precursor and product ions. The foregoing DDA technique may be repeated for isolating different precursors and obtaining a desired number of scans for the precursors and related product ions. In accordance with techniques herein with DDA and in manner similar to that as described above, the one or more precursors may be fragmented during a scan by ramping the CE within a single scan from a minimum to a maximum value. A determination may be made, such as using the conditions C1 and C2 described herein, as to whether the one or more precursors are being over fragmented and/or under fragmented and the CE minimum and maximum values may be accordingly adjusted.

It should be noted that the RT bin size may be the same as the scan time. In other words, an embodiment may use an RT bin size which corresponds to the same amount of time as the duration of an EE scan. An embodiment may use other RT bin sizes in accordance with techniques herein. In the case, for example, where the RT bin size is larger than the duration of an EE scan, the selected minimum CE and maximum CE may be performed for the duration of the RT bin. In such a case, the CE ramp (from minimum CE to maximum CE) for the single EE scan may be repeated for the duration of the RT bin time.

It should also be noted that FIG. 9, and also as described elsewhere herein provides an example of how the ramping of CE values, from minimum CE to maximum CE within a particular EE scan, may be determined in a linear fashion. In other words, the CE ramp may be linear and may be determined using linear interpolation techniques. As also mentioned elsewhere herein, the ramping of CE values within a particular EE scan may also be non-linear and may be determined using non-linear curve fitting techniques. For a given EE scan, an embodiment may determine the amount of time to spend in a particular portion of a CE range (e.g., portion of the CE range from CE minimum to CE maximum) based on a count or precursor frequency, based on precursor intensity or another measure indicating an abundance of particular precursors. For example, the amount of time in a particular portion of the CE range for a given EE scan may be proportional to the precursor intensity or other measure of precursor abundance associated with the particular portion. To further illustrate, assume a minimum CE=10 eV and a maximum CE=20 eV for a given EE scan. It may be determined using a particular metric that 75% of the precursors being fragmented occur within a particular m/z range and/or are at one or more charge states. It may also be determined that for these types of precursors, an optimal CE range is 12-15 eV. As such, an embodiment may determine the CE ramp for the EE scan in a piece-wise linear fashion so that a portion of the CE ramp provides for spending 75% of the EE scan time in the range is 12-15 eV. The remaining portions of the CE ramp from 10-12 eV and 15 eV to 20 eV may also be correspondingly weighted based on precursor intensity or other metric of other precursors having 10-12 eV and 15-20 eV as the preferred CE values for fragmentation.

An embodiment may determine optimum or preferred CE ramps such as, for example, particular samples, through iteratively performing the techniques herein and making repeated adjustments to CE values. Such iterative processing may terminate in accordance with one or more termination criteria. For example, such termination criteria may include terminating after a predetermined number of iterations, when no further CE adjustments or a minimum amount of CE adjustments are made, and the like. Once terminated, the determined preferred CE ramps may be stored in a lookup table or other structure and used in connection with selecting CE's for subsequently performed EE scans. For example, the techniques herein may be used to determine a lookup table based upon those tables and associated parameters/dimensions as illustrated in FIGS. 5A, 5B and 6. In the lookup tables, rather than have count, or intensity for each cell or entry as in FIGS. 5, 5B and 6, each entry may include information represented the previously determined optimum CE ramp for every m/z, RT and charge state bin. The CE ramp may be initially set in accordance with the CE range associated with the bin(s) (e.g., entries in the lookup table) containing the "most data" (e.g., highest precursor count or frequency, highest precursor intensities, or other metric regarding a precursor weighting factor).

Referring to FIGS. 9A and 9B, shown are exemplary sets of CE values (e.g., voltages) that may be used in determining an initial set of CE values in an embodiment in accordance with techniques herein. The initial set of CE values may then be accordingly adjusted using techniques herein. The values of 810 of FIG. 9A may be determined as optimal or desired CE values for a linear ramping of minimum CE and maximum CE values per charge state for an m/z range of 300-2000. The values of 820 of FIG. 9B may be determined as optimal or desired CE values using a non-linear or polynomial ramping of minimum and maximum CE values per charge state for an m/z range of 300-2000. Information of 810 and 820 may be provided, for example, by a vendor of an instrument performing mass spectrometry for use with techniques herein. The table 810 illustrates a set of CE values that may be used in determining an initial set of minimum and maximum CE values across EE scans having a linear curve (e.g., such as illustrated in FIG. 3B). In a similar manner, the table 820 illustrates a set of CE values that may be used in determining an initial set of minimum and maximum CE values across EE scans having a non-linear or polynomial-based curve.

Figure 9C:
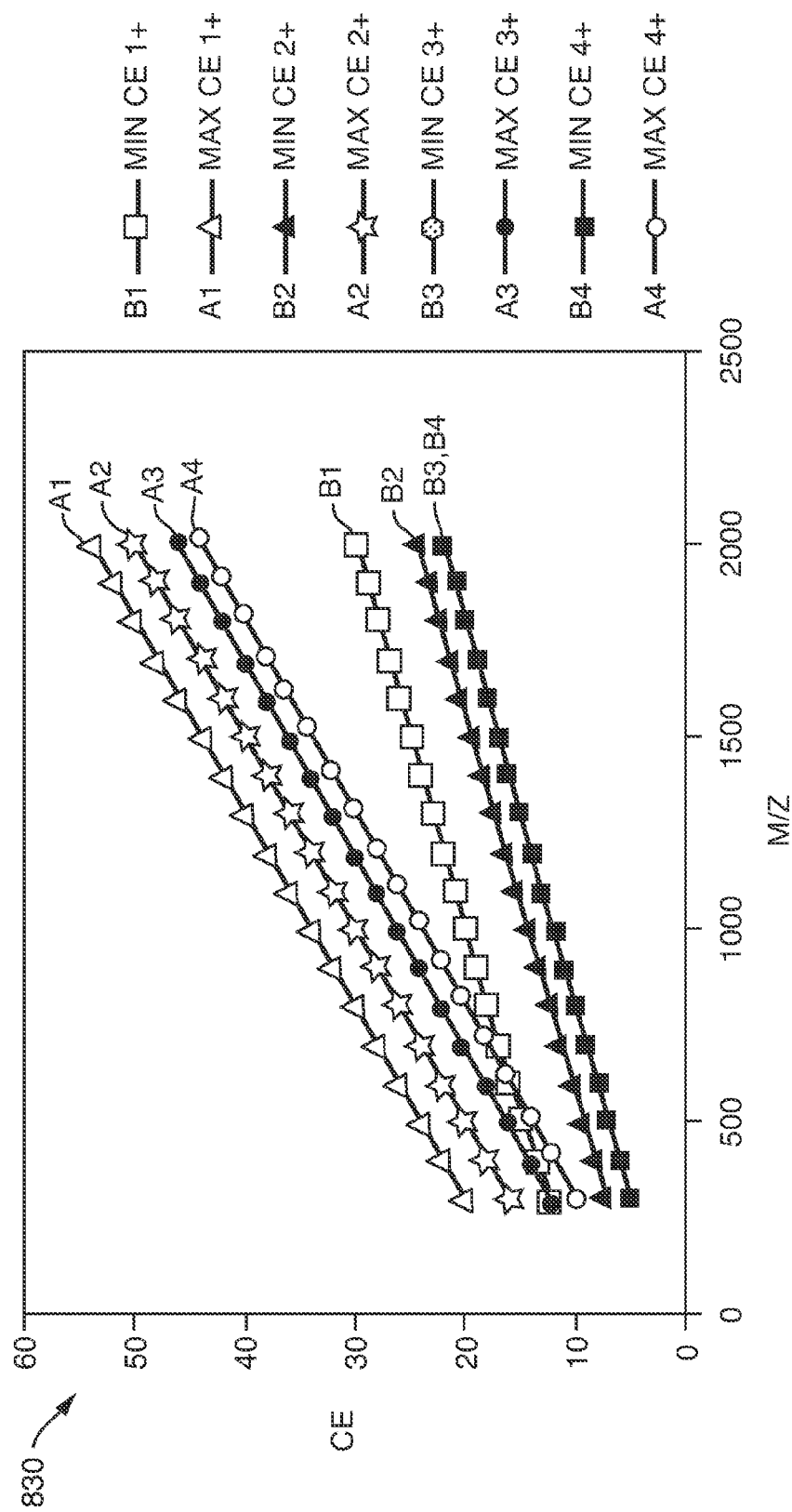

Referring to FIGS. 9C and 9D, shown are graphical representations of the data of FIGS. 9A and 9B. Graph 830 represents data from table 810 and graph 840 represents data from table 820.

As described above, the initial set of CE values may be used in accordance with techniques herein to produce spectra which may then be analyzed to determine any appropriate CE adjustments for one or more of the EE scans. As part of this analysis, an embodiment in accordance with techniques herein may also determine a distribution (e.g, such as based on intensity or frequency) for each combination of m/z value, charge state, and retention time. As an example, an embodiment may determine that 80% of the ions for a particular retention time are between 400-900 m/z at charge state=2. Using the data from table 820 of FIG. 9B, it may be determined that a desired CE range is between 8 and 36 as denoted, respectively, by elements 822 and 823. As such, the selected CE range for this retention time may be based on this range of between 8 and 36. For example, CE minimum may be selected as a value within several units of 8 and CE maximum selected as a value within several units of 36. Additionally, an embodiment may spend an amount of time within the CE range of 8-36 proportional to the amount of ions having the foregoing CE range as a desired CE range (e.g., may spend 80% of EE scanning time within the range of 8-36).

It should be noted that an embodiment in accordance with techniques herein may generally use any suitable technique and means for fragmentation besides a collision cell. For example, an embodiment may use electron transfer disassociation technique. The appropriate collision energies may vary with fragmentation techniques used in an embodiment. More generally, the techniques herein may be used to select CE values for use by a means for fragmentation. One particular technique used for fragmentation is a collision cell although other suitable means may also be used for fragmentation with the techniques herein.

An embodiment may optionally use the techniques described in U.S. Pat. No. 6,884,995, (the '995 patent) which is incorporated by reference herein, in combination with the techniques herein. For example, an embodiment may use an instrument operating in accordance with the techniques of '995 patent to obtain M/S data which is then processed using the techniques herein. An embodiment may also not utilize the techniques of the '995 patent when acquiring data analyzed using techniques herein. In such an embodiment, the techniques herein may also be used and may provide for improved selection of CE values.

An embodiment in accordance with techniques herein may also vary the cone voltage of the mass spectrometer as a function of time. The efficiency of ion transfer to the mass spectrometer, such as from an LC instrument, may be affected by the applied cone voltage at the inlet of the mass spectrometer. In-source fragmentation may occur if the cone voltage is set too high for ions entering into the mass spectrometer. In-source fragmentation occurs when ions are fragmented within the ionization source device of the mass spectrometer (e.g., element 214 of FIG. 2A). It is noted that as the mass or m/z increases, the amount of energy needed to draw the molecule into the mass spectrometer increases. As described elsewhere herein, the m/z of eluting ions tends to increase with time. Thus, as the retention time increases, the m/z tends to increase. Therefore, an embodiment may increase or vary the cone voltage as the retention time, and thus m/z or more generally ion mass as of a precursor, increases.

Figure 10:
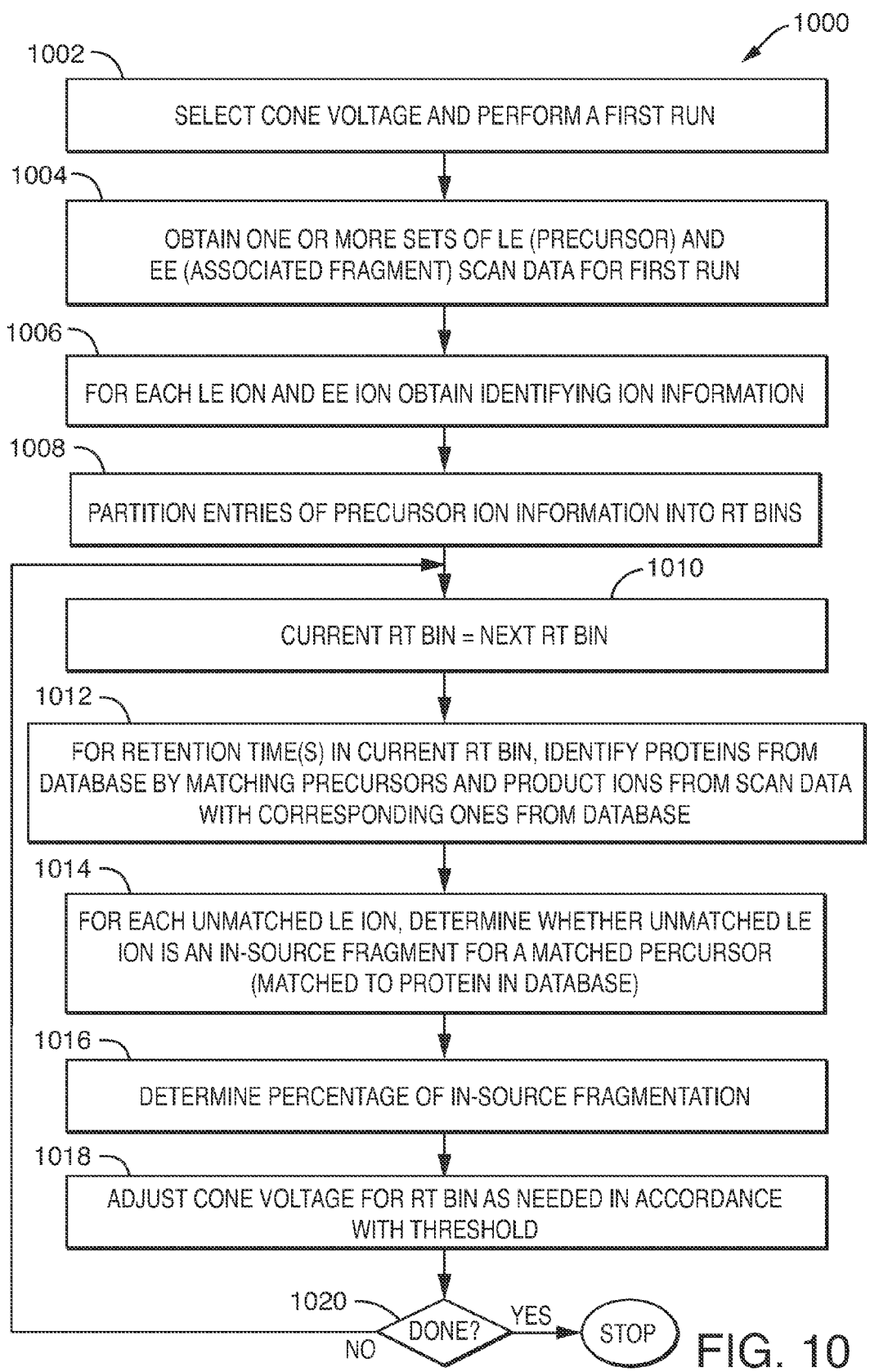
FIG. 10 is a flowchart of processing steps that may be performed in an embodiment in accordance with techniques herein to adjust cone voltages.

What will now be described with reference to FIG. 10 is how an embodiment may select cone voltages to be used at different points in time in connection with an experimental run of a sample such as in an LC-MS system. The steps of flowchart 1000 may be performed, for example, in an embodiment using the alternate scanning mode as described in the Bateman '130 patent or the modified version thereof described above where the CE is varied within each single EE scan. The selected cone voltage determined for a particular retention time may be used during both the EE and LE scans. The techniques herein for cone voltage selection may be used with any suitable scanning technique as described above for CE selection.

In step 1002, a single cone voltage or multiple cone voltages may be selected for use at different times during an experimental run analyzing a sample in an LC-MS system. The energy necessary to impart ion disassociation is generally a function of mass, z (charge state), and composition as is the applied cone voltage or ion entrance potential. If the potential is too high it will induce ion disassociation. If the potential is too low, the transfer efficiency (signal strength) of higher mass ions will decrease. As such in a typical LCMS acquisition, the set cone voltage may be characterized as a "compromise" having a value which, though low enough to minimize in-source fragmentation, is also however large enough for higher mass ions to enter the mass analyzer. Rather than have a set or fixed cone voltage, an embodiment in connection with the technique herein may ramp the cone voltage during gradient elution. At step 1004, a first run of analysis of the sample is performed such as using the alternate scanning mode as described in the Bateman '130 patent or the modified version thereof described above. As a result of the first run, one or more sets of LE (precursor) and EE (associated product or fragment) scan data are obtained. In step 1006, for each ion appearing in each LE scan and in each EE scan, obtain identifying ion information. An embodiment may obtain identifying ion information using techniques, such as described elsewhere herein in connection with step 508 of FIG. 4, and described in PCT Publication No. WO2007/140327 published Dec. 6, 2007 (PCT application no. PCT/US07/69784, international filing date May 25, 2007), ION DETECTION AND PARAMETER ESTIMATION FOR N-DIMENSIONAL DATA, Gorenstein, et al., which is incorporated by reference herein. As described above and in the foregoing PCT application, the ion information describing an ion may include the ion's retention time, mass-to-charge ratio or mass, charge state, and intensity. In step 1008, the ion information for precursors may form a set of entries (one entry per precursor) and such entries may be partitioned into RT bins as also described above.

Processing may then be performed for each of the RT bins. In step 1010, the variable current RT bin is assigned the next RT bin to be processed. In step 1012, for each retention time included in the current RT bin, proteins from a database matching those of the sample processed in the first run are identified. In accordance with one technique, a database may include protein profile information including data characterizing one or more precursors and associated fragments which are used to identify each protein catalogued in the database. Processing may be performed to determine a degree of similarity or correspondence between precursors and associated fragments included in the scan data for the first run and data stored in the database identifying proteins. PCT Publication No. WO2007/140251, published Dec. 6, 2007 (PCT application no. PCT/US07/069,657, international filing date May 24, 2007), APPARATUS AND METHOD FOR PERFORMING MASS SPECTROSCOPY, Geromanos et al., which is incorporated by reference herein, describes processing that may be performed in an embodiment to identify proteins in accordance with the identifying ion information for the scan data. At the end of step 1012, there may be one or more orphaned or unmatched ions from an LE scan containing data for the current RT bin where the unmatched ions have not been identified as matched with a particular protein from the database. For each unmatched ion in the LE scan, the unmatched ion may not be a precursor ion but may rather be an in-source fragment of an identified or matched precursor (matched to a protein as identified by the protein identification processing in step 1012). Therefore, in step 1014 for each unmatched ion of an LE scan, processing is performed to determine whether the unmatched ion is actually a fragment or product ion of one of the identified or matched precursors (matched to a protein in the database) having the same RT as the unmatched ion. Step 1014 processing may include determining a list of matched precursors (matched to a protein in the database) having the same retention time in the LE scan as the unmatched ion in the LE scan. For each matched precursor, there is a list of corresponding fragments from the database which may or may not have not been identified or matched to actual fragments in the EE scan data. The unmatched LE data, with their annotated apex retention-times, may be processed to see if any of them match within a predetermined mass error to any of the actual product ions from any identified precursor ions at the same or similar apex retention-times (e.g., within a predetermined retention time variance). In some instances, the matched status can be verified by the presence of unique product ions emanating from the breaking point of the parent precursor ion. For example, if, during the ion transfer (e.g., prior to the collision cell) approximately 40% of the precursor molecules lost three residues off the n-terminus, both the parent precursor ions as well as those emanating from the fragmentation process may be identified in the LE data. Traversing the collision cell, each precursor ion fragments producing y" and b ion fragment ion masses. Those from the true parent precursor ion match those found in the database. Though the in-source fragment (e.g., "shorter" version of the true parent precursor) is further fragmented and produces the same y" ion series as the true parent precursor, the b ion series is unique to the new n-terminus of the in-source fragment. These novel b ions may be used to determine that its parent precursor is actually an in-source fragment (of the true parent precursor).

At step 1016, a percentage of in-source fragmentation is determined. In one embodiment, this may be expressed for each RT bin as a ratio of:

sum intensity of all in-source fragments within the RT bin/ sum intensity for the RT bin.

In the foregoing the numerator represents an intensity of all ions within a single RT bin identified as an in-source fragment, and the denominator represents a sum intensity of all ions in the bin. It should be noted that the percentage value of in-source fragmentation represented above may also be further normalized in an embodiment in accordance with techniques herein. For example, an embodiment may take the percentage described above and further divide that quantity by a second ratio (with respect to a given RT bin) represented as:

sum of % intensities of parents of in-source fragments/ (100%−sum % intensities of parents of in-source fragments)

where each of the foregoing % intensities is a percentage relative to the total sum intensity for the RT bin. The numerator of the second ratio above may be determined by determining a first sum of the intensities of all the parents of the in-source fragments, determining a second sum intensity for the entire RT bin, and then dividing the first sum by the second sum.

At step 1018, the cone voltage for the RT bin is adjusted as needed in accordance with a threshold level of in-source fragmentation. In other words, the threshold level of in-source fragmentation may define an acceptable or expected level of such fragmentation. When the actual occurring in-source fragmentation as determined in step 1016 is not in line with the threshold level, the cone voltage may be adjusted by increasing or decreasing the cone voltage.

In one embodiment, the threshold level used in step 1018 may be empirically determined based on knowledge of existing systems and samples. The threshold level may be input by a user, defined as a default value in a system, or determined using other automated and/or manual techniques. The threshold level may be defined as a threshold window, for example 10%+/−5% so that when the in-source fragmentation is between 5% and 15%, no cone voltage adjustment is made. An embodiment may, of course, use other thresholds. If the in-source fragmentation % is less than (<) the threshold, then the cone voltage may be increased. If the in-source fragmentation % is more than (>) the same or a different threshold, then the cone voltage may be decreased. As an example, an embodiment may make the following adjustments:

If in-source fragmentation %<threshold1, then increase CV by 20%
If in-source fragmentation %>then threshold2, then decrease CV by 20%

In the foregoing, CV denotes "cone voltage". Threshold1 may be, for example 5% and threshold2 may be, for example 10%, and in-source fragmentation % may be the percentage determined in step 1016. It should be noted that the foregoing values used for threshold1, threshold 2, as well as the CV adjustments (e.g., increase and decrease) may vary than what is described above for purposes of illustration. The techniques herein should not be construed as limited to these and other values selected for purposes of illustration.

At step 1020, a determination is made as to whether all RT bins have been processed for the current set of scan data. If so, processing stops. Otherwise, control proceeds to step 1010 to continue processing the next RT bin. It should be noted that the processing of the flowchart 1000 performs a single iteration for cone voltage adjustments. Rather than stopping when step 1020 evaluates to yes, an embodiment may repeatedly perform the adjustment process for the same sample by resuming processing with step 1004 using the adjusted cone voltages and then making subsequently needed cone voltage adjustments. In other words, more generally, the cone voltages determined from iteration "n" for a sample may be used in performing a subsequent run "n+1" for the sample where the cone voltages from iteration "n" may be further adjusted in processing of iteration "n". An embodiment may perform the processing to evaluate and adjust the cone voltages a specified number of iterations, until there are no adjustments made to any cone voltages in step 1018 in an iteration, until there are a minimum number of cone voltage adjustments made, and the like. Repeatedly performing the processing may be characterized as tuning the cone voltage such as for a particular sample. If a different sample is then analyzed, the cone voltages may automatically be readjusted for use with the new sample by once again performing the steps of FIG. 10

As a result of using the techniques described above to determine and adjust the cone voltages, the cone voltage selected will increase with retention time.

Figure 11:
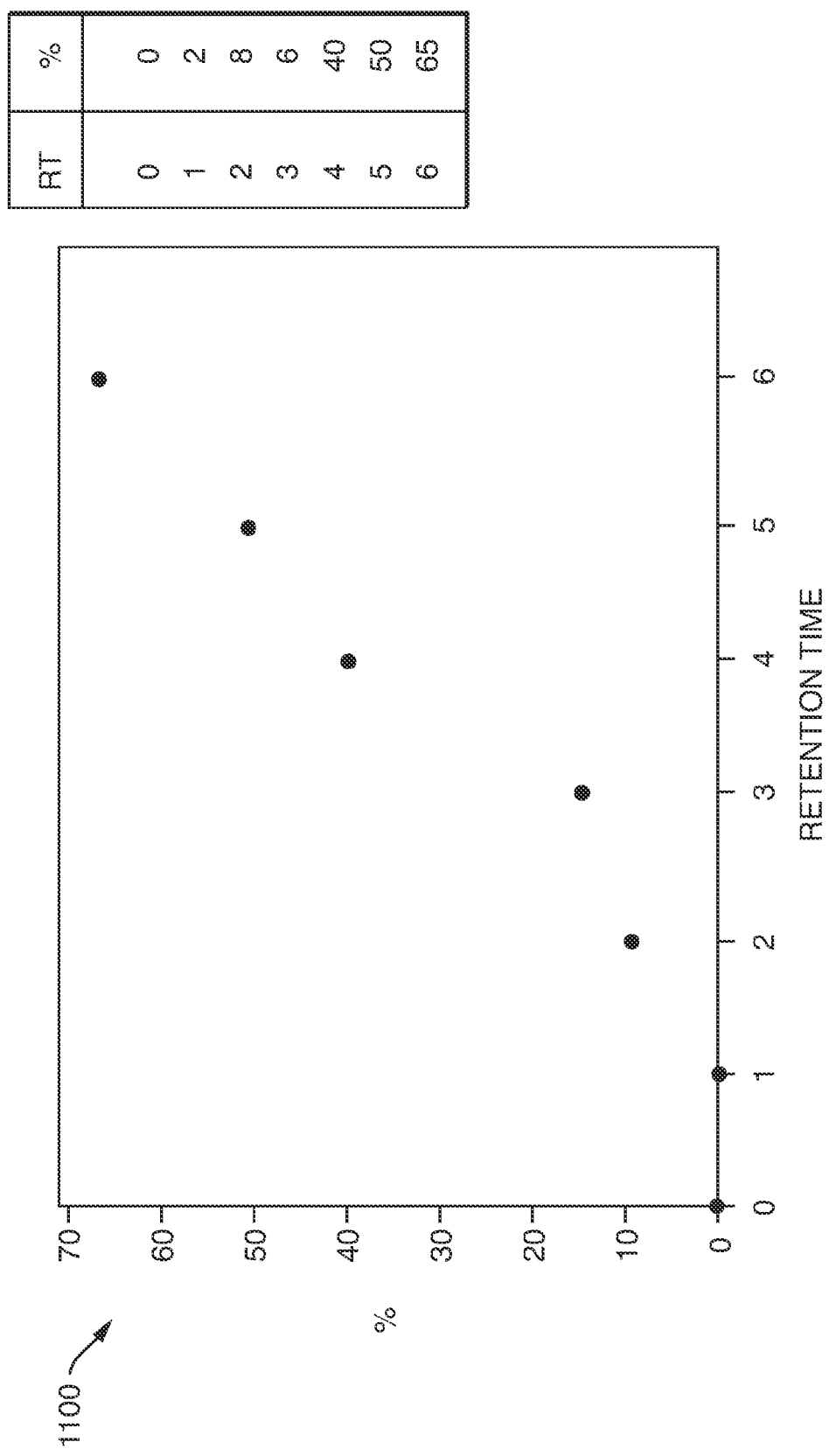
FIGS. 11 and 12 are examples illustrating use of the techniques herein in an embodiment in connection with evaluating in-source fragmentation and accordingly adjusting the cone voltage(s).

To further illustrate, reference is made to FIG. 11 including an exemplary graph of how the in-source fragmentation % values may be determined for each RT bin=1. Exemplary cone voltages used to generate the in-source fragmentation percentages of 1100 are described below. The example 1100 shows the in-source fragmentation %'s that may be determined as a result of analyzing data corresponding to a first run.

Figure 12:
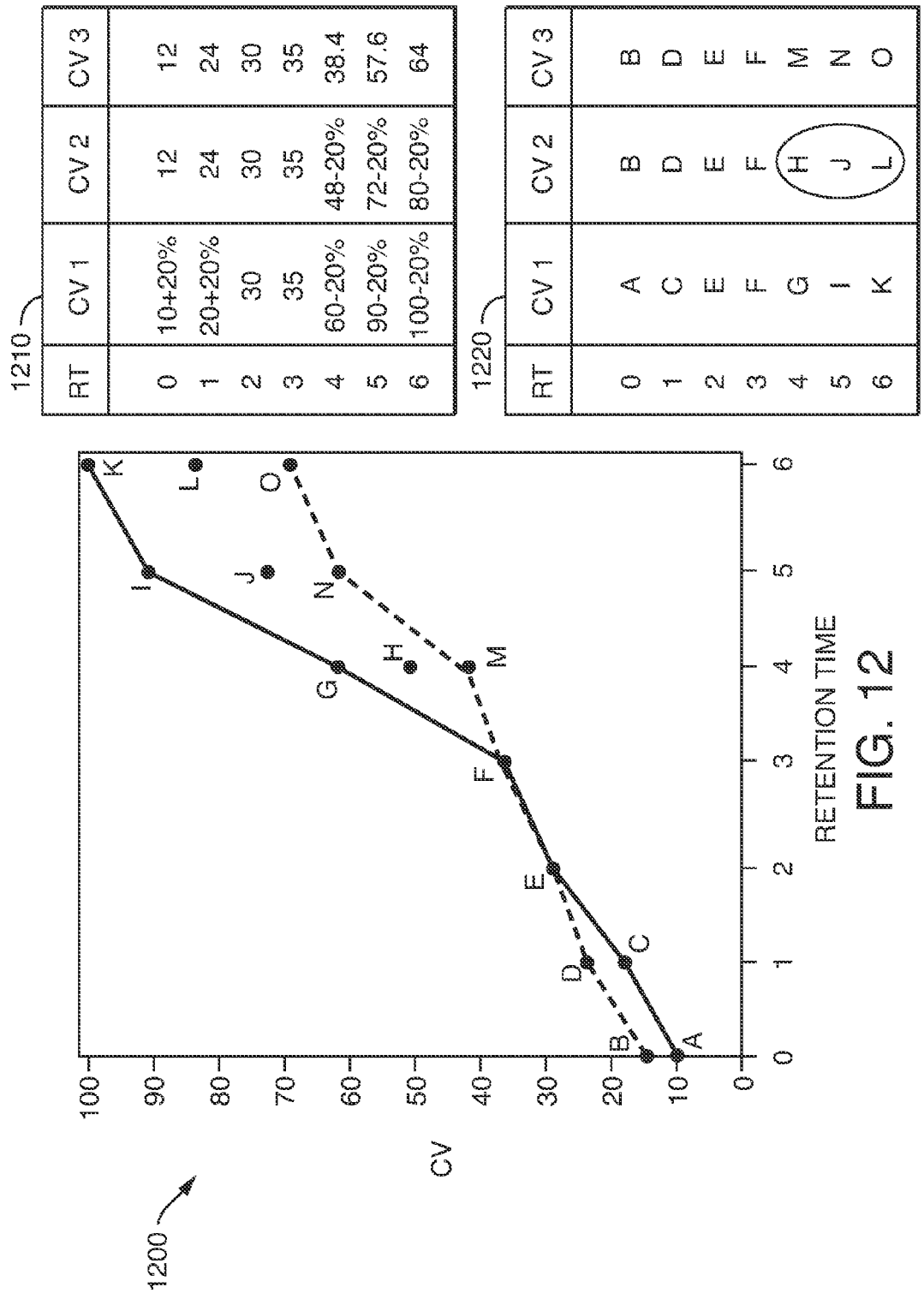

Referring to FIG. 12, shown is an example illustrating how the cone voltage may vary and be adjusted in accordance with techniques herein. The solid line may represent the initial set of cone voltages used on a first run (denoted CV1) which may be adjusted to produce a second set of cone voltages (denoted CV2). A second iteration of the processing described above may be performed using the second set of cone voltages and then adjusting this second set to produce a third set of cone voltages (denoted CV3). The dashed line may represent the set of cone voltages denoted CV3. The set of points H, J, and L denote cone voltage adjustments made in the second set which are then further adjusted to arrive at the third set of corresponding points, respectively, M, N, and O. Table 1210 lists the three sets of cone voltages and also denotes any increase such as a 20% CV increase, or decrease, such as a 20% CV decrease, to the cone voltages as determined using the techniques herein and using the exemplary adjustment rates described above.

The CV values may generally vary in manners similar to those described herein for CE values. For example, FIG. 12 illustrates that CV values may be varied across or between RT windows. Such variation of CV values between RT windows may be linear or non-linear. CV values may also be varied, linearly or non-linearly, within a single RT window from a starting to an ending CV. To further illustrate, CV values may vary as described and illustrated herein for CE values such as in connection with FIG. 9 so that CV values may vary between RT windows and also within each single RT window.

Also, as described above such as in connection with FIGS. 9A, 9B, 9C and 9D, an embodiment may use an initial set of CVs predetermined as optimal or desired for a given m/z and charge state. The initial set of CV values may be adjusted using the techniques described herein based on the amount of in-source fragmentation. One way in which an embodiment may vary the CVs is described above and further illustrated, for example, in FIG. 12. An embodiment may also vary the CVs within a particular RT window based on the distribution for a particular RT window as described above for CEs. For example, if 80% of the ions in an RT window are within the m/z range 400-900 and have charge state=2, then the CV values within the RT window may be varied, linearly or non-linearly, with an optimal CV range for these particular ions comprising the 80%.

In accordance with the above, the cone voltage may be varied as a function of time to enhance sensitivity of the MS for a broad spectrum of peptides throughout the LC-MS analysis. Using the techniques described above, cone voltages can be tuned or adjusted for use with a particular sample by performing one or more iterations of the processing described in FIG. 10 so that the cone voltage varies with retention time or, more generally, duration time of the experimental run analyzing the sample using mass spectrometry. The processing described above for cone voltage determination and selection may be performed using automated techniques such as by executing code on a computer system as described herein for collision energy voltages. Additionally, as also described above for collision energies, the computer system may also executed code to generate the appropriate control signals at the appropriate times to set the MS apparatus to the selected cone voltages.

It should be noted that an embodiment may use the techniques described herein in connection with the collision energy selection alone, or in combination with, those described herein in connection with the cone voltage selection.

In accordance with the foregoing descriptions, an embodiment may utilize time-dependent modulation of voltages to optimize the collision energy and/or cone voltage. An embodiment may control the CE voltage as a function of time for the LE scan control the CE voltage as a function of time for the minimum CE voltage used for an EE scan fragmenting precursors, control the CE voltage as a function of time for the maximum CE voltage used for an EE scan fragmenting precursors, and more generally, control the cone voltage as a function of time. The foregoing use of time may refer to the duration time of an experimental run or rather the increasing retention time during the experimental run.

An embodiment may use an initial set of CE values and/or CV values which are based on desired or optimally determined settings. More generally, an embodiment may also use any set of initial CE and/or CV values in accordance with techniques herein. Let, for example, a first initial set of CE and/or CV values be deemed "better than" a second initial set of CE and/or CV values. Some prior experimentation and knowledge may have gone into selecting the first initial set but not the second initial set. Either of the foregoing first or second initial sets may be used with the techniques herein. However, if the second initial set is used rather than the first initial set, the techniques herein may be performed for additional iterations in order to reach or converge at a set of acceptable final CE and/or CV values.

It should be noted that, although preceding paragraphs and exemplary embodiments apply the techniques described herein generally to peptides and proteins, the techniques herein are also well suited for use with any other molecules including, but not limited to metabolites, lipids, pesticides, natural products, and the like, whose ion entrance potential and/or fragmentation energies vary by any one or more of length, mass, charge-state, retention-time or mobility. As previously mentioned, existing systems not using the techniques herein may utilize static or single values for a CE and/or CV where such values are not varied as in an embodiment in accordance with techniques. Since not all molecules of varying or similar type behave identically during processing, an embodiment in accordance with the techniques herein may vary these energies (CE and/or CV) over time to maximize the information obtained as a result of sample analysis.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method for performing mass spectrometry comprising:
   generating a stream of one or more ions;
   transmitting said stream into a collision cell over a period of time; and
   selecting, in accordance with a set of criteria including a retention time of one or more precursor ions, a collision energy of the collision cell to generate one or more product ions for said one or more precursor ions in said stream, wherein the period of time corresponds to an amount of time of an elevated energy scan associated with producing said one or more product ions from said one or more precursor ions, and wherein, during said elevated energy scan, said collision energy is varied from a minimum setting to a maximum setting, and wherein the method further comprises:

evaluating, in accordance with one or more fragmentation criteria, whether said one or more precursor ions are sufficiently fragmented during said elevated energy scan when said collision energy is varied from said minimum setting to said maximum setting and adjusting said minimum setting and said maximum setting in accordance with said evaluating to generate, respectively, any one or more of an adjusted minimum setting and an adjusted maximum setting.

2. The method of claim 1, wherein said collision energy is selected in accordance with one or more sets of data respectively associated with said one or more precursor ions, each of said sets of data including a retention time, a mass or m/z value, and a charge state associated with one of said precursor ions.

3. The method of claim 1, wherein said collision energy is increased during said period of time from said minimum setting to said maximum setting, and wherein said collision energy is increased linearly during said period of time.

4. The method of claim 1, wherein said collision energy causes fragmentation of at least one ion.

5. The method of claim 1, wherein said minimum setting and said maximum setting are used in a first run with a sample and said adjusted minimum setting and said adjusted maximum setting are used in a subsequent run with said sample.

6. The method of claim 1, where said fragmentation criteria is used to determine whether one or more precursor ions having a same retention time are under fragmented and/or over fragmented.

7. The method of claim 1, wherein said fragmentation criteria includes a first indicator related to underfragmentation and a second indicator related to overfragmentation.

8. A method for performing mass spectrometry comprising:

generating a stream of one or more ions;

transmitting said stream into a collision cell over a period of time and selecting, in accordance with a set of criteria including a retention time of one or more precursor ions, a collision energy of the collision cell to generate one or more product ions for said one or more precursor ions in said stream, wherein the period, of time includes a first amount of time of a low energy scan during which collision energy is not varied, said low energy scan being associated with said one or more precursor ions, wherein, during the low energy scan, a spectrum for the first amount of time corresponds to said one or more precursor ions which are fragmented during a second amount of time included in said period of time when performing an elevated energy scan where said collision energy is varied during said second amount of time, and wherein said collision energy is increased during said second amount of time.

9. The method of claim 8, wherein the low energy scan is obtained when the collision cell operates in accordance with a low energy mode and the high energy scan is obtained when the collision cell operates in accordance with an elevated energy mode, wherein when in the low energy mode, a low voltage is applied to the collision cell and when in the high energy mode, a high voltage is applied to the collision cell.

10. The method of claim 9, wherein the low energy scan and the high energy scan are obtained when operating the collision cell by switching between the low energy mode and the elevated energy mode in accordance with a protocol that alternates application of the low energy mode and the elevated energy mode with a sufficient frequency whereby each of the low energy mode and the elevated energy mode is applied a plurality of times during a single chromatographic peak width.

11. The method of claim 8, wherein the stream of one or more ions are obtained from a protein included in a sample undergoing analysis.

* * * * *